(12) United States Patent
Griffin et al.

(10) Patent No.: US 6,310,082 B1
(45) Date of Patent: *Oct. 30, 2001

(54) BENZIMIDAZOLE COMPOUNDS

(75) Inventors: Roger J Griffin, Northumberland; Alan H Calvert; Nicola J Curtin, both of Tyne & Wear; David R Newell, Northumberland; Bernard T Golding, Newcastle Upon Tyne, all of (GB)

(73) Assignee: Newcastle University Ventures Limited, Newcastle Upon Tyne (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/594,776

(22) Filed: Jun. 16, 2000

Related U.S. Application Data

(63) Continuation of application No. 09/017,314, filed on Feb. 2, 1998, now Pat. No. 6,100,283, which is a continuation of application No. PCT/GB96/01832, filed on Jul. 30, 1996.

(30) Foreign Application Priority Data

May 30, 1909 (GB) ................................. 96112453
Aug. 2, 1995 (GB) ................................. 95158432

(51) Int. Cl.[7] ................... A61K 31/4184; C07D 235/08; C07D 235/12; C07D 235/18
(52) U.S. Cl. ................... 514/394; 548/304.4; 548/310.4; 548/310.7
(58) Field of Search ................... 514/394; 548/304.4, 548/310.4, 310.7

(56) References Cited

U.S. PATENT DOCUMENTS

| | | | |
|---|---|---|---|
| 3,795,680 | 3/1974 | Burton et al. | 260/309.2 |
| 5,216,003 | 6/1993 | Vazquez | 514/381 |
| 5,314,880 | 5/1994 | Whittaker et al. | 514/80 |
| 5,554,632 | 9/1996 | Teuber et al. | 514/338 |
| 5,735,973 | 4/1998 | Sasahara et al. | 148/269 |

FOREIGN PATENT DOCUMENTS

| | | |
|---|---|---|
| 148431 | 7/1985 | (EP) . |
| 209707 | 1/1987 | (EP) . |
| 719765 | 7/1996 | (EP) . |

OTHER PUBLICATIONS

Gilchrist et al, J. Chem. Soc., Perkin Trans. 1 (1979), (9), 2303–7.
Griffin et al, CA 125:189126 (1996).

*Primary Examiner*—Laura L. Stockton
(74) *Attorney, Agent, or Firm*—Pillsbury Winthrop LLP

(57) ABSTRACT

Benzimidazole-4-carboxamide compounds (I) which can act as potent inhibitors of the DNA repair enzyme poly(ADP-ribose) polymerase or PARP enzyme (EC 2.4.2.30), and which thereby can provide useful therapeutic compounds for use in conjunction with DNA-damaging cytotoxic drugs or radiotherapy to potentiate the effects of the latter. In formula (I), R and R' may each be selected independently from hydrogen, alkyl, hydroxyalkyl (e.g. $CH_2CH_2OH$), acyl (e.g. acetyl or benzoyl) or an optionally substituted aryl (e.g. phenyl) or aralkyl (e.g. benzyl or carboxybenzyl) group. R is generally a substituted phenyl group in the most preferred compounds. The compounds may also be used in the form of pharmaceutically acceptable salts or pro-drugs.

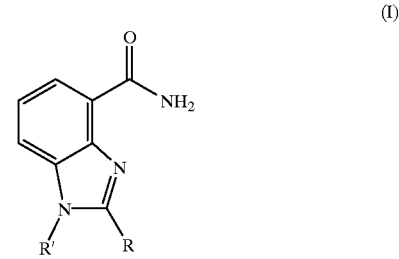

(I)

21 Claims, 1 Drawing Sheet

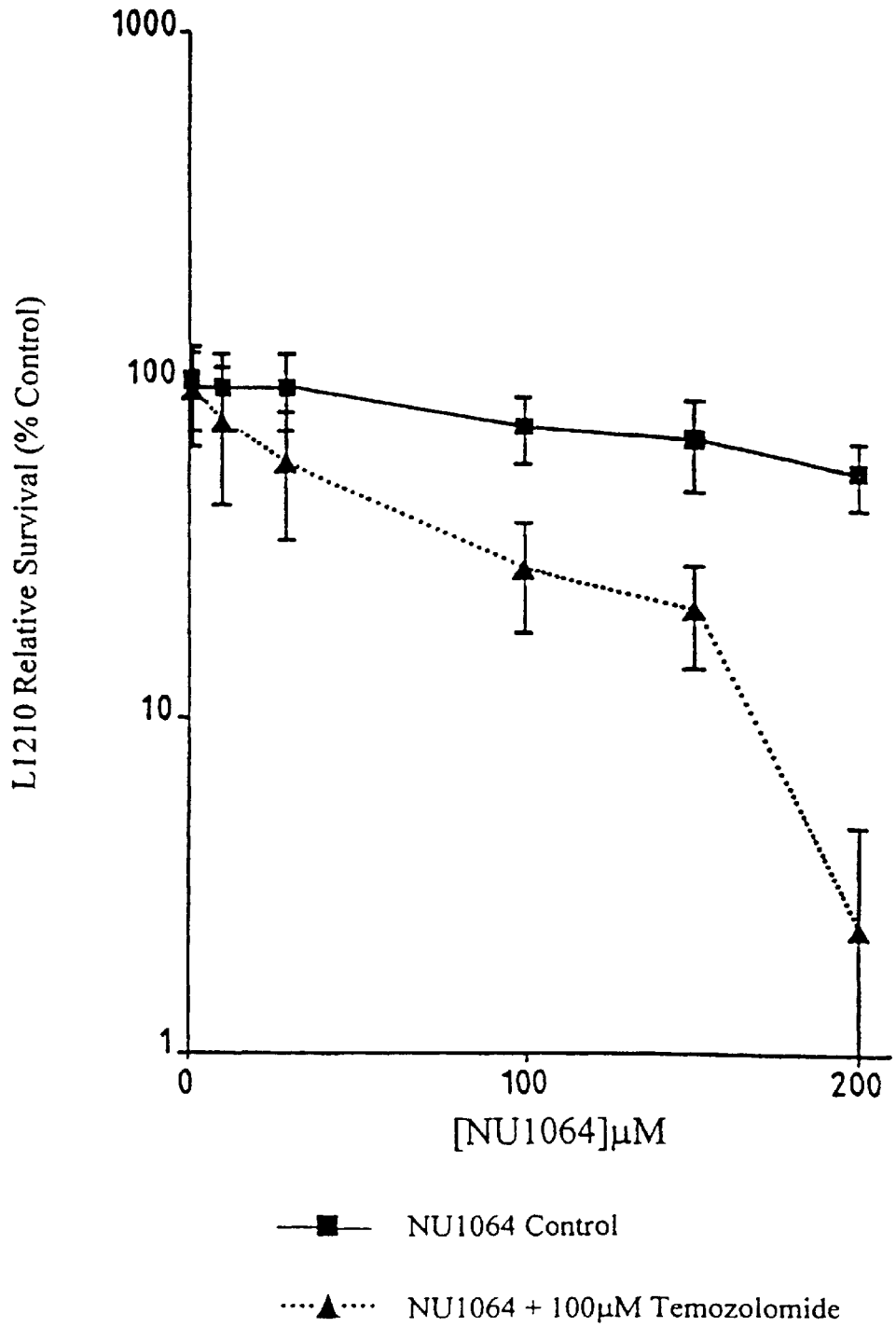

BENZIMIDAZOLE COMPOUNDS

This is a continuation of application Ser. No. 09/017,314, filed Feb. 2, 1998, now U.S. Pat. No. 6,100,283, which is a continuation of PCT/GB96/01832, filed Jul. 30, 1996.

The present invention relates to certain benzimidazole compounds that are of interest as being at least potentially useful chemotherapeutic agents by Virtue of an ability to inhibit the activity of the enzyme poly ADP-ribosyltransferase (EC 2.4.2.30), also known as poly(ADP-ribose) polymerase, commonly referred to as ADPRT or PARP. In general, the latter abbreviation, PARP, will be used throughout the present specification.

BACKGROUND

At least in higher organisms, the enzyme poly ADP-ribosyltransferase is known to catalyse a transfer of the ADP-ribose moiety from the oxidized form, NAD+, of nicotinamide adenine dinucleotide to nuclear acceptor proteins so as to form homo ADP-ribose polymers, and this process has been implicated in a number of cellular events such as, for example, repair of DNA damage, development of cellular differentiation, transformation of cells by oncogenes, and gene expression. A common feature in a number of these processes is the formation and repair of DNA strand breaks and the stage which involves the PARP enzyme appears to be that of DNA ligase II-mediated strand rejoining. In the majority of cases a role for poly ADP-ribosylation has been implicated by the use of inhibitors of the PARP enzyme, and this has led to suggestions that such inhibitors, by interfering with the intracellular DNA repair mechanism, may have a useful chemotherapeutic role insofar as they should be able to modify treatment resistance characteristics and potentiate or enhance the effectiveness of cytotoxic drugs in chemotherapy or of radiation in radiotherapy where a primary effect of the treatment is that of causing DNA damage in target cells, as for example in any forms of antitumour therapy.

In this connection, several classes of PARP inhibitors are already known, including benzamide and various nicotinamide and benzamide analogues, especially 3-substituted benzamides with small substituent groups such as 3-amino, 3-hydroxy and 3-methoxy. PARP inhibitory activity of certain N-substituted benzamides has also been reported in EP-A-0305008 wherein it has also been proposed to use these compounds in medicine for increasing the cytotoxicity of radiation or of chemotherapeutic drugs.

Regarding this use of benzamide compounds as chemotherapeutic agents, various studies on such compounds that are known to exhibit PARP inhibitory activity have confirmed that they can potentiate the cytoxicity of a range of antitumour agents in vitro, for example, bleomycin and methylating drugs. More limited data has further indicated that such benzamide compounds can also potentiate the activity of cytotoxic drugs in vivo, although the dose requirements have appeared to be rather high (e.g. in the region of 0.5 g kg$^{-1}$ per dose for 3-aminobenzamide) and there may be associated problems in preparing satisfactory pharmaceutical formulations and in avoiding toxicity limitations. Furthermore, a number of the known benzamide compounds have also been shown clearly to have potential as radiosensitizers, increasing for example ionising radiation-induced tumour cell kill both in vitro and in vivo, and it is believed that in many cases this effect is related to these compounds acting as PARP inhibitors and interfering with DNA repair.

However, notwithstanding the existing data from in vitro and in vivo studies suggesting that PARP inhibitors have considerable potential as useful chemotherapeutic agents which merit further clinical evaluation, for instance in connection with cancer therapy, currently available known PARP inhibitors are not considered as yet to be entirely suitable to represent candidate drugs and there remains a need to find and develop a greater range of compounds having potentially useful PARP inhibitory properties.

DISCLOSURE OF THE INVENTION

The present invention identifies a new range or ranges of compounds of interest as PARP inhibitors that can be useful in medicine, especially when administered in conjunction with at least certain cytotoxic drugs or with radiotherapy for increasing the cytotoxic effectiveness thereof. In general, the compounds to which this invention relates comprise certain benzimidazole derivatives, more particularly benzimidazole-4-carboxamide compounds, as hereinbelow defined. By virtue of their structure it would appear that many such compounds are particularly well adapted to compete with the natural substrate NAD+ for the PARP enzyme.

More specifically, from one aspect, the invention resides in the use of a compound as herein defined for the manufacture of a medical or veterinary preparation for use in therapy for inhibiting activity of the enzyme poly(ADP-ribose)polymerase or PARP (also known as ADP-ribosyl transferase or ADPRT), such enzyme inhibition constituting an element of a therapeutic treatment, wherein said compound provides the active PARP enzyme inhibiting agent and comprises a benzimidazole-4-carboxamide having the general structural formula I

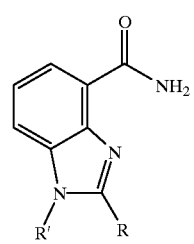

or a pharmaceutically acceptable salt and/or pro-drug form thereof, characterised in that in structural formula I R is selected from hydrogen, alkyl, hydroxyalkyl (e.g. CH$_2$CH$_2$OH), acyl (e.g. acetyl or benzoyl) and an optionally substituted aryl (e.g. phenyl) or aralkyl (e.g. benzyl or carboxybenzyl) group, and R' is selected from hydrogen, alkyl, hydroxyalkyl (e.g. CH$_2$CH$_2$OH), acyl (e.g. acetyl or benzoyl) and an optionally substituted aryl (e.g. phenyl) or aralkyl (e.g. benzyl or carboxybenzyl) group.

The invention also provides for use in therapy, as active pharmaceutical substances, especially but not exclusively as PARP inhibitors, benzimidazole compounds having the general structural formula I

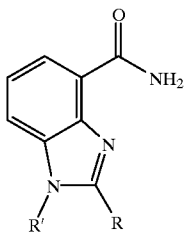

(or a pharmaceutically acceptable salt and/or pro-drug form thereof), with substituents as defined above except for provisos that R does not represent 4'-methane-sulphonyloxy-2'-methoxyphenyl or 4'-methane-sulphonylamino-2'-methoxyphenyl and does not represent a phenyl group having a substituent which is an alkylsulphenyl, alkylsulphinyl, alkanesulphonyl or alkylsulphoximino group, an alkylsulphoximino group substituted at the nitrogen atom by an alkanoyl, alkylsulphonyl or hydroxycarbonyl-alkylenecarbonyl group, an ethoxy or n-propoxy group each of which is substituted in the terminal position by an alkylsulphenyl, alkylsulphinyl, alkanesulphonyl or alkylsulphoximino group, an alkoxycarbonylamino or an N-alkylaminocarbonyl-amino group and R' is not an optionally substituted aralkyl group and does not include a biphenyl or substituted biphenyl group.

The invention further provides novel benzimidazole compounds having the general structural formula I (or a pharmaceutically acceptable salt and/or pro-drug form thereof), with substituents as defined immediately above except for the further proviso that R does not represent an unsubstituted aryl group such as phenyl.

Alkyl groups when present as such or as a moiety in other groups will generally be composed of 1–8 carbon atoms, preferably 1–6 carbon atoms, and more usually 1–4 carbon atoms. In particular, when R and/or R' is an alkyl group this will generally be $C_{1-6}$ alkyl, such as for example methyl, ethyl, n-propyl, i-propyl, n-butyl, t-butyl or cyclohexyl. When R and/or R' is or includes a phenyl group this may be substituted, especially in the 4 (para) position but alternatively or additionally in the 2-position and/or 3-position for instance, by various substituents including hydroxy, alkoxy (methoxy or ethoxy for example), cyano, carboxy, amide, tetrazole, amino or substituted amino, $CW_3$ (e.g. $CF_3$) or W where W is halogen.

In cases where R' is hydrogen or alkyl preferred compounds of structural formula I include compounds in which R is phenyl or benzyl having at least one substituent in the benzene ring which is selected from hydroxy, alkoxy, $NO_2$, $N_3$, $NR_5R_6$ ($R_5$ and $R_6$ each being independently hydrogen, alkyl or alkoxy), $NHCOR_3$ ($R_3$ being alkyl or aryl), $CO_2R_4$ ($R_4$ being H or alkyl), an amide (e.g. $CONH_2$), tetrazole, alkyl, hydroxyalkyl, $CW_3$ or W (W being halogen), and CN.

More particularly, where R represents a substituted phenyl group having the structural formula II

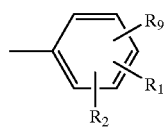

$R_1$, $R_2$ and $R_9$ may be each selected independently from H, hydroxy, alkoxy, $NO_2$, $N_3$, $NR_5R_6$ ($R_5$ and $R_6$ each being independently hydrogen, alkyl or alkoxy), $NHCOR_3$ ($R_3$ being alkyl or aryl), $CO_2R_4$ ($R_4$ being H or alkyl), an amide (e.g. $CONH_2$), tetrazole, alkyl, hydroxyalkyl, $CW_3$ or W (W being halogen), and CN.

The invention also includes a process for preparing a compound of structural formula I as specified above wherein R represents an optionally substituted phenyl group having the structural formula II, said process comprising the steps of reacting an alkyl 2,3-diaminobenzoate with an aryl acid chloride, treating the product with acetic acid at an elevated temperature to bring about benzimidazole ring formation, and reacting with liquid ammonia to form the amide derivative.

Where R' represents a substituted phenyl group having the structural formula III

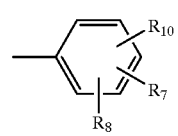

$R_7$, $R_8$ and $R_{10}$ may be each selected independently from H, hydroxy, alkoxy, $NO_2$, $N_3$, $NR_5R_6$ ($R_5$ and $R_6$ each being independently hydrogen, alkyl or alkoxy), $NHCOR_3$ ($R_3$ being alkyl or aryl), $CO_2R_4$ ($R_4$ being H or alkyl), an amide (e.g. $CONH_2$), tetrazole, alkyl, hydroxyalkyl, $CW_3$ or W (W being halogen), and CN.

Compounds of structural formula I as hereinabove defined which have an aromatic ring that includes a CN substituent may often also be particularly useful as intermediates in making other compounds in accordance with the invention since a cyano substituent can generally be converted, using standard methodology, into a variety of other functional groups, including amine, carboxyl, amide and tetrazole.

Within the ranges of benzimidazole compounds disclosed herein, preferred members which are of particular interest include (a) 2-methylbenzimidazole-4-carboxamide;
(b) benzimidazole-4-carboxamide;
(c) 2-phenylbenzimidazole-4-carboxamide;
(d) 2-(4'-methoxyphenyl)benzimidazole-4-carboxamide;
(e) 2-(4'-trifluoromethylphenyl)benzimidazole-4-carboxamide;
(f) 2-(4'-hydroxyphenyl)benzimidazole-4-carboxamide;
(g) 2-trifluoromethylbenzimidazole-4-carboxamide;
(h) 2-(4'-methoxyphenyl)-N-methylbenzimidazole-4-carboxamide;
(i) 2-(4'-nitrophenyl)benzimidazole-4-carboxamide;
(j) 2-(4'-cyanophenyl)benzimidazole-4-carboxamide;
(k) 2-(3'-trifluoromethylphenyl)benzimidazole-4-carboxamide;
(l) 2-(3'-methoxyphenyl)benzimidazole-4-carboxamide;
(m) 2-(4'-methoxyphenyl)-1-N-benzoylbenzimidazole-4-carboxamide,
(n) 2-(4'-aminophenyl)benzimidazole-4-carboxamide
(o) 2-(2'-trifluoromethylphenyl)benzimidazole-4-carboxamide,
(p) N-carboxybenzyl-2-(4'-methoxyphenyl)-benzimidazole-4-carboxamide.

In the above-mentioned compounds of this invention wherein there is an electron-rich aromatic ring, it is believed that in at least some cases the carboxamide group may be constrained in a fixed conformation, particularly favourable for presenting the compound as an inhibitor of NAD+ binding to the PARP enzyme, by an intramolecular hydrogen bond between an imidazole ring nitrogen atom and one of the hydrogen atoms of the carboxamide group.

As already indicated, the invention also embraces or extends to methods of preparing compounds as hereinbefore defined (including intermediates in some cases) and to the therapeutic use of such compounds in treating mammals. This includes their use for making medical or veterinary preparations or pharmaceutical formulations containing an effective PARP inhibitory amount of the active compound for administration to a patient in conjunction with a cytotoxic drug or radiotherapy in order to increase the cytotoxic effectiveness of the latter. Such preparations or formulations may be made up in accordance with any of the methods well known in the art of pharmacy for administration in any suitable manner, for example orally, parenterally (including subcutaneously, intramuscularly or intravenously), or topically, the mode of administration, type of preparations or formulation and the dosage being generally determined by the details of the associated cytotoxic drug chemotherapy or radiotherapy that is to be enhanced.

In making up such pharmaceutical formulations in the form of sterile liquid preparations for parental use for instance, a predetermined therapeutically effective non-toxic amount of the particular compound concerned may be dissolved in phosphate buffered saline and the preparations may be presented in unit dosage form and contained in sealed ampoules ready for use. In general, at least in aqueous solution, concentrations not greater than 200 mg/ml will be preferred, but the amount and dosage routine required for optimum effectiveness will of course vary and is ultimately at the discretion of the medical or veterinary practitioner treating the mammal concerned in each particular case. Where the compound is to be used in conjunction with a cytotoxic drug, the latter in some cases may be administered simultaneously and may be conveniently incorporated in the same pharmaceutical formulation or composition.

As indicated, the compounds according to this invention have at least potential as PARP inhibitors, and in vitro tests hereinafter described have demonstrated positive pharmacological activity which it is believed reflects the activity to be found in vivo in the course of therapeutic clinical use.

It will be understood that where reference is made in this specification to compounds of formula I such reference should be construed as extending also to their pharmaceutically acceptable salts and to other pharmaceutically acceptable bioprecursors (pro-drug forms) where relevant. The term "pro-drug" is used in the present specification to denote modified forms or derivatives of a pharmacologically active compound which biodegrade in vivo and become converted into said active compound after administration, especially oral or intravenous administration, in the course of therapeutic treatment of a mammal. Such pro-drugs are commonly chosen because of an enhanced solubility in aqueous media which helps to overcome formulation problems, and also in some cases to give a relatively slow or controlled release of the active agent.

A satisfactory pro-drug must generally be a water-soluble derivative which is non-toxic and reasonably stable in solution at physiological pH but which will biodegrade or convert, e.g. by enzymatic degradation or by an enviromental pH change, to the active compound at the location required following administration in the course of therapy. For the benzimidazole compounds of the present invention, pro-drug forms may conveniently be provided by carbamate or amino acid derivatives, e.g. glycine or other amino-acid carbamate derivatives, or by phosphate derivatives. Phosphate derivatives may be susceptible to enzymic dephosphorylation in vivo and are presently preferred, especially water-soluble ammonium or alkali metal phosphate salts. These may often be conveniently prepared from compounds of structural formula I having at leastone hydroxyl group substituent, e.g. in an aromatic ring component of R, by reacting with a dibenzyl phosphonate, preferably in the presence of a tertiary base such as N,N-diisopropylethylamine.

In cases where R is phenyl (or benzyl) and where it is necessary to have a substituent other than hydroxyl, e.g. $NO_2$, $CO_2H$, CN etc. at the 4' position in order to give satisfactory PARP inhibitory activity, a hydroxyl substituent amenable to phosphorylation or other pro-drug modification may be provided at another aromatic ring position, e.g. at the 3' position.

In all the water-soluble pro-drug forms presently envisaged the phosphate, carbamate or other water-solubilizing pro-drug moiety will be a component of R or R' in structural formula I.

It should also be understood that where any of the compounds referred to can exist in more than one enantiomeric form, all such forms, mixtures thereof, and their preparation and uses are within the scope of the invention.

BRIEF DESCRIPTION OF THE DRAWING

The invention is illustrated by reference to the accompanying drawing wherein:

FIG. 1 is a graph showing results obtained using the invention.

DESCRIPTION OF EXAMPLES OF PREFERRED EMBODIMENTS

The following examples and descriptions of stages in synthetic routes of preparation of various preferred compounds of interest serve to further illustrate the present invention, but should not be construed in any way as a limitation thereof.

In the first example (EXAMPLE 1), the preparation is described of various intermediate compounds required for the preparation of benzimidazole compounds in accordance with the present invention which are described in EXAMPLES 2 to 6.

EXAMPLE 1

Preparation of Intermediate Compounds
(a) 3-Nitrophthalamic Acid

3-Nitrophthalic anhydride (10.0 g, 50 mmol) was added in portions over 20 minutes to concentrated aqueous ammonia solution (15 ml), and the mixture was stirred at 30° C. for a further 30 minutes. The crystalline mass of ammonium phthalamate, deposited upon cooling the pale yellow solution, was collected and redissolved in a minimum amount of warm water. Concentrated hydrochloric acid (4.5 ml) was added dropwise, with stirring, and the resulting paste was washed with water, and dried in vacua to give 3-nitrophthalamic acid as a fine white powder. (9.01 g, 83%), m.p. 217° C. Found: C, 45.76; H, 2.79; N, 13.21. $C_8H_6N_2O_5$ requires C, 45.71; H, 2.86; N, 13.33%; $v^{max}$/$cm^{-1}$ 3466.52, 3321.84, 1668.64, 1604.98, and 1525.89; $\delta_H$ (d$_6$-DMSO, 200 MHz) 7.75 (1H, br s, CONH), 7.8 (1H, t, Ar-5H), 8.16 (1H, brs, CONH), 8.2 (1H, d, Ar-6H), 8.3 (1H, d, Ar-4H); $\delta_C$ (d$_6$-DMSO) 127.32, 130.06, 132.28, 133.49, 134.78, 147.71, 166.25, and 166.60; m/z (EI) 192 (M+−1), 177, 149, 103, 75.

(b) 2-Amino-3-nitrobenzoic Acid (3-nitroanthranilic acid)

To a stirred solution of potassium hydroxide (24.1 g) in water (110 ml) at 0° C. was added bromine (2.46 ml), followed by 3-nitrophthalamic acid 10 g, 47.62 mmol). The reaction mixture was stirred for 3 hours at 60° C., cooled to room temperature, and stirred for a further 12 hours. The orange precipitate was collected, redissolved in a minimum amount of water, and acidified by the dropwise addition of concentrated hydrochloric acid. Recrystallisation of the resulting yellow solid from hot water afforded 3-nitroanthranilic acid as yellow microcrystals (6.42 g, 74%), m.p. 208–209° C. Found: C, 45.83; H, 3.07; N. 15.21. $C_7H_6N_2O_4$ requires C, 46.15; H, 3.29; N, 15.38%; $v^{max}$/cm$^{-1}$ 3476.17, 3344.99, 3094.21 and 1687.93; $\delta_H$ (d$_6$-DMSO, 200 MHz) 6.76–6.84 (1H, t, Ar-5$\underline{H}$), 8.29–8.41 (2H, dd, Ar-4/6$\underline{H}$), 8.60 (2H, s, Ar—N$\underline{H}_2$), 13.4–14.0 (1H, br s, Ar—CO$_2\underline{H}$); $\delta_C$ (d$_6$-DMSO) 113.19, 131.97, 140.02 (Ar-4/5/6$\underline{C}$H), 115.02 (Ar—$\underline{C}$—NH$_2$), 132.77 (Ar—$\underline{C}$—CO$_2$H), 147.09 (Ar—$\underline{C}$—NO$_2$), 168.95 (Ar—$\underline{C}$O$_2$H); m/z (EI) 182 (M$^+$), 164.

(c) Methyl 2-amino-3-nitrobenzoate

Hydrogen chloride gas was bubbled through a solution of 2-amino-3-nitrobenzoic acid (0.5 g, 2.75 mmol) in methanol (40 ml) for 15 minutes at 0° C. The reaction mixture was heated under reflux for 5 hours, and allowed to cool to room temperature over a further 12 hours, whereupon methyl 2-amino-3-nitrobenzoate was deposited as a yellow solid (417 mg, 77%), m.p. 95–96° C. Found: C, 49.09: H, 3.78; N, 14.03. $C_8H_8N_2O_4$ requires C, 48.98; H, 4.08; N, 14.29%; $v^{max}$/cm$^{-1}$ 3452.5, 3316.9, 1702, and 1253.7; $\delta_H$ (d$_6$-DMSO, 200 MHz) 3.95 (3H, s, OC$\underline{H}_3$), 6.79–6.87 (1H, t, Ar-5$\underline{H}$), 8.28–8.33 (1H, dd, Ar-4$\underline{H}$), 8.41–8.46 (1H, dd, Ar-6$\underline{H}$), 8.45–8.46 (2H, br s, Ar—N$\underline{H}_2$); m/z (EI) 196 (M$^+$), 164, 118, 90, 63.

(d) 2,3-Diaminobenzoic Acid

Palladium on carbon catalyst (10% Pd, ~200 mg) was added cautiously, as a slurry in methanol (10 ml), to a solution of 3-nitroanthranilic acid (2.44 g, 13 mmol) in methanol (120 ml), and the mixture was stirred under a hydrogen atmosphere for 2 hours until the absorption of gas ceased. The catalyst was removed by filtration through Celite, and the filtrate was evaporated to dryness under reduced pressure to afford the crude product. Purification by column chromatography on silica gel, with dichloromethane:methanol (4:1) as eluent, gave 2,3-diaminobenzoic acid as a red solid (1.34 g, 66%). $v_{max}$/cm$^{-1}$ 3433.73, 2882.02, 2602.30 and 1658.99; $\delta_H$ (d$_6$-DMSO, 200 MHz) 5.8–7.4 (4H, br s, 2×N$\underline{H}_2$), 6.45 (1H, t, Ar-5$\underline{H}$), 6.75 (1H, d, Ar-4$\underline{H}$), 7.20 (1H, d, Ar-6$\underline{H}$); $\delta_C$ (d$_6$-DMSO) 110.31, 115.45, 118.33, 120.55, 135.03, 140.36, 170.68; m/z (EI) 152 (M$^+$), 134, 106, 79.

(e) Methyl 2,3-diaminobenzoate

A solution of 2,3-diaminobenzoic acid (0.2 g, 1.32 mmol) in methanol (40 ml) was saturated with hydrogen chloride as described above, and the mixture was subsequently heated under reflux for 2 hours. The solid residue obtained on evaporation of the solvent was dissolved in water, and the solution was adjusted to pH 7.0 with sodium hydrogen carbonate. After extraction with ethyl acetate (2×30 ml), the combined organic layers were dried (MgSO$_4$), and the solvent was removed to give methyl 2,3-diaminobenzoate as a brown oil which solidified on trituration with petrol (40/60) (121.6 mg, 56%), m.p. 62–63° C. Found: C, 58.35; H, 5.80; N, 16.69. $C_8H_{10}N_2O_2$ requires C, 57.83; H, 6.02; N, 16.87%; $\delta_H$ (d$_6$-DMSO), 200 MHz) 3.87 (3H, s, OC$\underline{H}_3$). 4.90 (2H, br s, Ar-2-N$\underline{H}_2$), 6.32 (2H, br s, Ar-3-N$\underline{H}_2$), 6.46–6.54 (1H, t, Ar-5$\underline{H}$), 6.80–6.84 (1H, dd, Ar-4$\underline{H}$), 7.18–7.23 (1H, dd, Ar-6$\underline{H}$); m/z (EI) 166 (M$^+$), 134, 106, 79.

Methyl 2,3-diaminobenzoate was also prepared by reduction of methyl 2-amino-3-nitrobenzoate as follows: a solution of methyl $^2$-amino-3-nitrobenzoate (284 mg, 1.45 mmol) in methanol (40 ml), containing palladium on carbon catalyst (10% Pd, ~50 mg), was stirred under hydrogen for 24 hours. The solution was filtered through Celite to remove the catalyst, and the solvent was evaporated in vacuo to afford the methyl ester as a brown solid. (180 mg, 75%) identical to methyl 2,3-diaminobenzoate prepared above.

(f) Methyl 2-amino-3-N-benzoylaminobenzoate

A solution of benzoyl chloride (38.4 μl, 0.331 mmol) in tetrahydrofuran (5 ml) was added dropwise to a solution of methyl 2,3-diaminobenzoate (50 mg, 0.301 mmol) in dry tetrahydrofuran (5 ml), containing triethylamine (46 μl) and 4-dimethylaminopyridine (1.8 mg, 5 mol %). After stirring the mixture for 24 hours at 45° C., solvents were evaporated, and the crude product was purified by column chromatography on silica gel, with petrol (40/60); ethyl acetate (3:2) as eluent. Recrystallisation from ethyl acetate-petrol (40/60), gave the title compound as white crystals. (60 mg, 74%); $\delta_H$ (d$_6$-DMSO, 200 MHz) 3.95 (3H, s, OC$\underline{H}_3$), 6.64 (2H, br s, Ar—N$\underline{H}_2$), 6.69–6.77 (1H, t, Ar-5$\underline{H}$), 7.46–7.50 (1H, d, Ar-4$\underline{H}$), 7.59–7.70 (3H, m, Ph-3 and Ph-3' 4$\underline{H}$), 7.81–7.85 (1H, d, Ar-6$\underline{H}$), 8.11–8,14 (2H, d, Ph-2$\underline{H}$ and Ph-2'$\underline{H}$), 9.8–9.9 (1H, br, s, Ar—N$\underline{H}$CO); m/z (EI) 270 (M$^+$), 253, 105.

(g) Methyl 2-amino-3-N-(4'-methoxybenzoyl) aminobenzoate

To a solution of methyl 2,3-diaminobenzoate (460 mg, 2.77 mmol) in dry tetrahydrofuran (20 ml) was added 4-methoxybenzoyl chloride (378 μl, 2.77 mmol), triethylamine (385.5 μl, 2.77 mmol), and 4-dimethylaminopyridine (17 mg, 5 mol %). The reaction mixture was stirred at room temperature overnight, yielding an insoluble precipitate that was collected by filtration. The filtrate was evaporated under reduced pressure and the residual solid was redissolved in boiling methanol, and hot filtered to remove the insoluble material. The solvent was removed in vacuo, and the solid residue was combined with the previously collected precipitate. Recrystallisation from aqueous methanol afforded white crystals of the title compound. (513.2 mg, 62%); mp 179–180° C.; Found: C, 64.26; H, 5,31; N, 9.17. $C_{16}H_{16}N_2O_4$ requires C, 64.0; H, 5.33; N, 9.33; $v_{max}$/cm$^{-1}$ 3425.54, 3341.54, 3277.84, 1699.24, 1632.12, 1251.11; $\delta_H$ (d$_6$DMSO, 200 MHz) 3.92 (3H, s, OMe), 3.94 (3H, s, OMe), 6.59 (2H, s, Ar—N$\underline{H}_2$), 6.68–6.75 (1H, t, Ar-5$\underline{H}$), 7.13–7.17 (2H, d, J=8.8, Ph-3/3'$\underline{H}$), 7.43–7.46 (1H, d, Ar-4$\underline{H}$), 7.79–7.83 (1H, d, Ar-6$\underline{H}$), 8.07–8.12 (2H, d, J=8.8, Ph-3.3' $\underline{H}$), 9.7 (1H, br s, —N$\underline{H}$CO—); $\delta_C$ (d$_6$DMSO) 51.98, 55.76, 110.62, 113.79, 114.67, 125.0, 126.84, 129.12, 130.14, 133.20, 147.36, 162.21, 165.74, 168.33; m/z (EI) 300 (M+), 135, 107, 77.

(h) Methyl 2-phenylbenzimidazole-4-carboxylate

A solution of methyl 2-amino-3-N-benzoylaminobenzoate (6.3 mg, 0.023 mmol) in glacial acetic acid (0.5 ml) was stirred under reflux for 15 minutes. After cooling, the solvent was removed under reduced pressure to afford the title compound; $\delta_H$ (d$_6$-DMSO, 200 MHz) 4.09 (3H, s, OC$\underline{H}_3$), 7.40–7.48 (1H, t, Ar-5$\underline{H}$), 7.64–7.70 (3H, m, 2-Ph-3$\underline{H}$ and 3'-Ph-4$\underline{H}$), 7.93–7.97 (1H, d, Ar-4$\underline{H}$), 8.06–8.10 (1H, d, Ar-6$\underline{H}$), 8.39–8.41 (2H, d, 2-Ph-2/2'$\underline{H}$), 12.4–12.5 (1H, br, s, Ar—N$\underline{H}$CO).

EXAMPLE 2

Benzimidazole-4-carboxamide (Compound NU1066)

(a) 1st Stage—Preparation of Benzimidazole-4-carboxylic Acid (Compound NU1067)

A mixture of 2,3-diaminobenzoic acid (0.5 g, 3.29 mmol) and formic acid (405 μl, 9.87 mmol) in hydrochloric acid (4M, 10 ml) was heated under reflux for one hour. The precipitate which formed on cooling was collected, redissolved in boiling methanol, and decolorised with activated charcoal. Evaporation of the solvent gave benzoxazole-4-carboxylic acid as a white powder (407.9 mg, 77%) Found: C, 46.11; H, 3.63; N, 13.27. $C_8H_6N_2O_2 \cdot HCl \cdot 0.5\ H_2O$ requires C, 46.28; H, 3.88; N, 13.49%; $\delta_H$ (d6-DMSO, 200 MHz) 7.7–7.8; (1H, t, Ar-5$\underline{H}$), 8.2–8.3 (2H, dd, Ar-4/6$\underline{H}$), 9.65 (1H, s, imidazole-2$\underline{H}$).

(b) 2nd Stage—Preparation of Benzimidazole-4-carboxamide (Compound NU1066)

A suspension of benzimidazole-4-carboxylic acid (3.97.4 mg, 2.45 mmol) in thionyl chloride (10 ml) was heated under reflux for 3.5 hours, and the thionyl chloride was removed by vacuum distillation. The residual solid was suspended in dry tetrahydrofuran (10 ml) and added dropwise to concentrated aqueous ammonia (50 ml) with stirring over 30 minutes. Excess solvent was removed in vacuo, and the residue was dissolved in a minimum volume of water and extracted with ethyl acetate (2×20 ml). The solid recovered on evaporation of the combined organic layers was dissolved in hydrochloric acid (0.1M, 10 ml) and the insoluble precipitate was removed by filtration. The aqueous filtrate was carefully adjusted to pH 9 in increments of 1 pH unit, and ethyl acetate extractions (10 ml) were undertaken at each step. The combined extracts were dried ($MgSO_4$) and the solvent was evaporated. Recrystallisation from ethyl acetate furnished benzimidazole-4-carboxamide (50 mg, 13%) Found: C, 59.95; H, 3.90; N, 24.59. $C_9H_7N_3O$ requires C, 59.63; H, 4.35; N, 26.09%; uv/nm 210, 270, 291; $v_{max}$/cm$^{-1}$ 3321.84, 3150.16, 1747.73, 1680.21; $\delta_H$ (d$_6$-DMSO, 200 MHz) 7.4 (1H, t, Ar-5$\underline{H}$), 7.8–8.0 (3H, dd, Ar-4/6$\underline{H}$), 8.5 (1H, br s, imidazole-2$\underline{H}$), 9.4 (1H, br s, CON$\underline{H}$), 13.1 (1H, br s, CON$\underline{H}$); m/z (EB) 161 (M$^+$), 141, 116, 99.

EXAMPLE 3

2-Methylbenzimidazole-4-carboxamide (Compound NU1064)

(a) 1st stage—Preparation of 2-Methylbenzimidazole-4-carboxylic Acid

Acetic acid (0.23 ml) was added to a solution of 2,3-diaminobenzoic acid (200 mg, 1.32 mmol) in hydrochloric acid (4M, 3.2 ml) and the mixture was refluxed for 1 hour. Solvents were evaporated and the residual solid was redissolved in boiling methanol (5 ml) iand decolorised with activated charcoal. Removal of the solvent furnished 2-methylbenzimidazole-4-carboxylic acid as an amorphous white solid (167.5 mg, 72%); $\delta_H$ (d$_6$-DMSO) 2.9 (3H, s, imidazole-2-C$\underline{H}_3$), 7.6–7.8 (1H, t, Ar-5$\underline{H}$) 8.1 (2H, d, Ar-4/6 $\underline{H}$); m/z (EI 176 (M$^+$), 158, 130.

(b) 2nd stage—Preparation of 2-Methylbenzimidazole-4-carboxamide (Compound NU1064)

A suspension of 2-methylbenzimidazole-4-carboxylic acid (500 mg, 2.84 mmol) in thionyl chloride (10 ml) was heated under reflux for 2 hours, and the thionyl chloride was removed by vacuum distillation. The solid residue was redissolved in dry tetrahydrofuran, and added dropwise to concentrated aqueous ammonia solution (50 ml) over 30 minutes, with stirring. The solvent was removed under vacuum, and the solid residue was redissolved in a minimum of hot water, filtered, and extracted with ethyl acetate (2×30 ml). Evaporation of the solvent afforded a brown solid which was recrystallised from ethyl acetate to give the title compound as a white solid (70.1 mg, 14%) Found: C, 61.47; H, 4.96; N, 23.39. $C_9H_9N_3O$ requires C, 61.71; H, 5.14; N, 24.0%; uv/nm 209, 270; $v_{max}$/cm$^{-1}$ 3296.77, 3071.07, 1913.63, 1859.62, 1805.60; $\delta_H$ (d$_6$-DMSO, 200 MHz) 2.68 (3H, s, imidazole-2-C$\underline{H}_3$), 7.30–7.38 (1H, t, Ar-5$\underline{H}$), 7.72–7.46 (1H, d, Ar-4$\underline{H}$), 7.86–7.90 (1H, d, Ar-6$\underline{H}$), 7.72–7.90 (1H, br s, imidazole-N$\underline{H}$), 9.4 (1H, br s, CON$\underline{H}$), 12.8 (1H, brs, CON$\underline{H}$); m/z (EI) 175 (M$^+$), 158, 130.

EXAMPLE 4

2-Phenylbenzimidazole-4-carboxamide (Compound NU1070)

(a) 1st Stage—Preparation of 2-phenylbenzimidazole-4-carboxylic Acid

A mixture of 2,3-diaminobenzoic acid (0.1 g, 0.66 mmol), benzoic acid (80.2 mg, 0.66 mmol) and polyphosphoric acid (~5 ml) was heated at 150–160° C. for 30 minutes, and, after cooling, crushed ice (~10 g) was added. Insoluble materials were removed from the dark solution by filtration, and the filtrate was extracted with ethyl acetate (2×20 ml) to remove unreacted benzoic acid. The aqueous solution was cautiously neutralised with sodium hydroxide (10 M), filtered, and the filtrate was extracted with ethyl acetate (2×30 ml). The combined extracts were dried ($MgSO_4$) and the solvent was evaporated. Chromatography on silica gel, with dichloromethane:methanol (85:15) as eluent, gave the title compound (31.2 mg, 20%); $\delta_H$ (d$_6$-DMSO, 200 MHz) 7.4 (1H, t, Ar-5$\underline{H}$), 7.62 (3H, br s, 3-Ph-4$\underline{H}$ and 3'-Ph-4$\underline{H}$), 7.91 (1H, d, Ar-6$\underline{H}$), 7.97 (1H, d, Ar-4$\underline{H}$), 8.39 (2H, d, Ph-2$\underline{H}$ and Ph2'-$\underline{H}$); m/z (EI) 238 (M$^+$), 220, 192, 77.

(b) 2nd Stage—Preparation of 2-phenylbenzimidazole-4-carboxamide (NU1070)

2-Phenylbenzimidazole-4-carboxylic acid (50 mg, 0.21 mmol) was dissolved in dry tetrahydrofuran (10 ml) and thionyl chloride (16.8 μl, 0.231 mmol) and DMF (0.05 ml) were added. The mixture was stirred at room temperature for 12 hours, when a white precipitate developed, and the suspension was added dropwise to stirred aqueous ammonia (10 ml) over 10 minutes. The mixture was stirred for a further 30 minutes, diluted with water (20 ml), and neutralised with hydrochloric acid (4M). The white solid which was precipitated upon cooling, was collected by filtration to afford 2-phenylbenzimidazole-4-carboxamide (31 mg, 62%); $v_{max}$/cm$^{-1}$ 3320, 3180, 1660 and 1600; $\delta_H$ (d$_6$-DMSO, 200 MHz) 7.45 (1H, t, Ar-5$\underline{H}$), 7.72 (3H, d, 3-Ph-4 $\underline{H}$), 7.87 (1H, d, Ar-4$\underline{H}$), 7.97 (1H, br s, CON$\underline{H}$), 7.99 (2H, d, Ar-6$\underline{H}$), 8.38 (2H, d, Ph-2-$\underline{H}$ and Ph-2-$\underline{H}$); 9.5 (1H, br s, CON$\underline{H}$); m/z (EI) 237 (M$^+$), 220, 192, 165, 77.

EXAMPLE 5

2-(4'-Methoxyphenyl)benzimidazole-4-carboxamide (NU1076)

(a) 1st Stage—Preparation of Methyl 2-(4'-methoxy-phenyl)benzimidazole-4-carboxylate Acetate Salt Methyl 2-amino-3-N-(4'-methoxybenzoyl)benzoate (480 mg, 1.6 mmol) was dissolved in glacial acetic acid (15 ml), and heated at 120°–130° C. for 30 minutes. The solvent was removed and the solid residue was recrystalised from ethyl acetate-petrol (40/60) to yield the product as a white crystalline solid. (409 mg, 75%); mp 141–142° C.; Found: C, 63.68; H, 4,79; N, 7.88; $C_{16}H_{14}N_2O_3 \cdot CH_3CO_2H$ requires C, 63.16; H, 5.26; N, 8.19; $v_{max}$/cm.$^{-1}$ 3375.33, 1718.46, 1696.80, 1282.81, 1257.81, 1257.34; $\delta_H$ (d$_6$DMSO), 200 MHz) 2.02 (3H, s, C$\underline{H}_3$CO$_2$H), 3.97 (3H, s, OMe), 4.09 (3H, s, OMe), 7.21–7.25 (2H, d, J=8.6, Ph-3/3'$\underline{H}$), 7.39–7.46 (1H, t, Ar-5$\underline{H}$), 7.90–7.93 (1H, d, Ar-4$\underline{H}$), 8.00–8.04 (1H, d, Ar-6 $\underline{H}$), 8.36–8.40 (2H, d, J=8.6, Ph-2/2'$\underline{H}$), 12.1 (1H, s, Imz-$\underline{H}$), 12.3–12.4 (1H, br, s, CH$_3$CO$_2\underline{H}$); $\delta_C$ (d$_6$DMSO) 21.35, 52.37, 55.64, 114.41, 121.68, 122.35, 124.34, 129.56, 153.63, 161.27, 166.13, 172.37; m/z (EI) 282 (M⁺—CH₃CO₂H), 250, 222, 77, 60, 43, 32.

(b) 2nd Stage—Preparation of 2-(4'-Methoxypheny) benzimidazole-4-carboxamide (NU1076)

The acetate salt of methyl (2-(4'-methoxy-phenyl) benzimidazole-4-carboxylate was dissolved in excess liquid ammonia and heated at 100° C. in a sealed pressure vessel at 40 atmospheres overnight. The ammonia was allowed to evaporate, and the solid residue was collected and washed with ice cold water (3×5 ml). Recrystallisation from aqueous methanol afforded the title compound (226.4 mg, 80%); mp 261–263° C.; Found: C, 66.07; H, 4.23; N, 15.29. $C_{15}H_{13}N_3O_2$. $0.2CH_3OH$ requires C, 66.70; H, 5.08; N, 15.35; $v_{max}/cm^{-1}$ 3321.47, 3140.72, 1656.23, 1608.25, 1421.43, 1242.55; $\delta_H$ (d₆DMSO, 200 MHz) 3.96 (3H, s, OMe), 7.23–7.27 (2H, d, J=8.6, Ph-3/3'H), 7.37–7.45 (1H, t, Ar-5H), 7.78–7.82 (1H, d, Ar-4H), 7.87 (1H, br s, Imz-H), 7.93–7.96 (1H, d, Ar-6H), 8.27–8.31 (2H, d, J=8.6, Ph-2/2' H), 9.4–9.5 (1H, br s, —CONH), 13.3–13.4 (1H, br s, —CONH); m/z (EI) 267 (M⁺), 249, 222, 206, 77, 32.

EXAMPLE 6

2-(4'-trifluoromethyl)benzimidazole-4-carboxamide (NU1077)

(a) 1st Stage—Preparation of Methyl 2-amino-3-N-(4'-trifluoromethylbenzoyl)aminobenzoate To a solution of methyl 2,3-diaminobenzoate (300 mg, 1.807 mmol) was added 4-trifluoromethylbenzoyl chloride (268.4 μl, 1.807 mmol), triethylamine (251.4 μl, 1.807 mmol) and 4-dimethylaminopyridine (11 mg, 5 mol %), and the mixture was stirred at room temperature overnight. The reaction solvent was removed under reduced pressure and the resulting solid was washed with ethyl acetate. Recrystallisation twice from methanol-water gave the title compound as a white solid. (83.6 mg, 14%); mp 180–181° C.; Found: C, 56.75; H, 3.50; N, 8.28. $C_{16}H_{13}F_3N_2O_3$ requires C, 56.80; H, 3.85; N, 8.28; uv/nm 222; $\delta_H$ (d₆DMSO, 200 MHz) 3.93 (3H, s, OMe), 6.70–6.76 (3H, m, Ar-5H, Ar—N H₂), 7.46–7.49 (1H, d, Ar-4H), 7.81–7.85 (1H, d, Ar-6H), 7.99–8.03 (2H, d), 8.29–8.33 (2H, d), 10.05 (1H, s, —N HCO—); m/z (EI) 338 (M⁺), 321, 289, 145, 32.

(b) 2nd Stage—Preparation of Methyl 2-(4'-trifluoromethylphenyl)benzimidazole-4-carboxylate Acetate Salt Methyl 2-amino-3-N-(4'-trifluoromethylbenzoyl) aminobenzoate (75.7 mg, 0.224 mmol) was dissolved in glacial acetic acid (5 ml) and stirred at 125° C. for 0.5 hour. The solvent was evaporated and the remaining white solid was washed with petrol (40/60) to yield the title compound. (59.6 mg, 70%); mp 138–140° C.; Found: C, 56.78; H, 3.98; N, 7.36; $C_{16}H_{11}F_3N_2O_2CH_3CO_2H$ requires C, 56.84; H, 3.94; N, 7.37. uv/nm 206, 319; $\delta_H$ (d₆-DMSO, 200 MHz) 2.01 (3H, s, CH₃CO₂H), 7.44–7.52 (1H, t, Ar-5H), 7.97–8.14 (4H, m), 8.65–8.66 (2H, d), 12.1 (br s, Imidazole-NH), 12.7–12.8 (1H, br s, CH₃CO₂H); m/z (EI) 320 )M⁺—CH₃CO₂H), 301, 288, 260, 145, 60, 43.

(c) 3rd Stage—Preparation of 2-(4'-trifluoromethyl) benzimidazole-4-carboxamide (NU1077)

The acetate salt of methyl 2-(4'-trifluoromethylphenyl) benzimidazole-4-carboxylate was dissolved in excess liquid ammonia and heated at 100° C., in a sealed pressure vessel at 40 atmospheres, for 12 hours. The ammonia was allowed to evaporate, and the solid residue was washed with ice cold water (3×5 ml). Recrystallisation from methanol-water yielded the product as fine white needles. (19.1 mg, 48%); mp 301–305° C.; Found: C, 56.45; H, 3.50; N, 12.41. $C_{15}H_{10}F_3N_3O.CH_3OH$ requires C, 56.97; H, 4.18; N, 12.46; $\delta_H$ (d₆-DMSO, 200 MHz) 7.45 (1H, t, Ar-5H), 7.88–7.92 (1H, d, Ar-4H), 7.99 (1H, br s imidazole-NH), 8.03 (1H, d, Ar-6H); 8.06–8.10 (2H, d, J=8.1), 8.55–8.59 (2H, d, J=8.1), 9.3–9.4 (1H, br s, —CONH), 13.7–13.8 (1H, br s, —CON H); m/z (EI) 288 (M⁺—NH₃), 260, 69.

EXAMPLE 7

2-(4'-Hydroxyphenyl)-1-H-benzimidazole-4-carboxamide (Compound NU1085)

Under an argon atmosphere 1M boron tribromide in dichloromethane (3.8 ml, 3.79 mmol) was transferred to a flask containing 2-(4'-methoxyphenyl)benzimidazole-4-carboxamide (NU 1076 from Example 5) (202.4 mg, 0.758 mmol). The resulting solution was refluxed for 24 hours using an air condenser. The solvent was removed by distillation to complete dryness. The solid residue was treated with 10% NaOH (10 ml), followed by dropwise addition of concentrated hydrochloric acid to neutralise (pH 7). The white precipitate was collected by filtration and dissolved in ethyl acetate (0 ml). The organic solvent was washed with water (2×3 ml), dried over MgSO₄, and the product was obtained by removal of the solvent under reduced pressure. (109.5 mg, 57%). mp 266–267° C.; Found C 63.27, H 4.37, N 15.67 $C_{14}H_{11}N_3O_2.0.75$ MeOH requires C 63.04 H 4.69 N 15.76; $v_{max}(cm^{-1})$ 3424.01, 3384.16, 3309.20, 3249.55, 3155.62, 1642.35, 1618.02, 1594.50, 1577.74; $\delta_H$ 7.03–7.07 (2H, d, J=8.5), 7.34–7.42 (1H, t), 7.75–7.79 (1H, d), 7.85 (1H, br s), 7.90–7.94 (1H, d), 8.15–8.19 (2H, d, J=8.5), 9.4–9.6 (1H, br s), 10.0–10.4 (1H, br s), 13.0–13.4 (1H, br s); m/z (EI) 253 (M⁺), 236, 208, 93.

EXAMPLE 8

2- (4' -Methoxyphenyl)-1-methylbenzimidazole-4-carboxamide (Compound NU1090)

2-(4'-Methoxyphenyl)benzimidazole-4-carboxamide (NU1076 from Example 5) (105.3 mg, 0.394 mmol) and powdered potassium hydroxide (22 mg, 0.394 mmol) were suspended in acetone (4 ml) and stirred until all the solids had dissolved. Methyl iodide (24.6 μll, 0.394 mmol) was added and the reaction stirred at room temperature overnight. The solvent was removed under reduced pressure and the white solid residue purified by column chromatography with dichloromethane/methanol 95:5 to give fine white crystals of the title compound. (33.2 mg, 30%) mp 289–292° C.; Found C 68.62 H 5.36 N 14.67 $C_{16}Hl_5N_3O_2$ Requires C 68.33 H 5.34 N 14.95; $v_{max}(cm^{-1})$ 3309.23, 3141.44, 1671.29, 1605.30, 1255.08, $\delta_H$ 3.95 (3H, s), 4.02 (3H, s), 7.22–7.27 (2H, d), 7.44–7.52 (1H, t), 7.86–8.00 (5H, m), 9.4 (1H, br s, NH); m/z (EI) 281 (M⁺), 264, 250.

EXAMPLE 9

2-(4'-Methoxyphenyl)-1-benzoylbenzimidazole-4-carboxamide (Compound NU1101)

A solution of 2-(4'-Methoxyphenyl)benzimidazole-4-carboxamide (NU1076 from Example 5) (75.1 mg, 0.281 mmol) and powdered potassium hydroxide (15.8 mg, 0.281 mmol) was prepared in acetone (3 ml) and stirred until all the solids had dissolved. Benzoyl chloride (32.6 μl, 0.281 mmol) was added and the solution stirred overnight at room temperature, with the production of a white precipitate. The solvents were removed under reduced pressure, and the white residue was purified by column chromatography using dichloromethane/methanol 95:5. The resulting solid was recrystallised from petrol 40/60/ethyl acetate to give the pure product as brilliant white prisms. (15.6 mg, 15%). mp 207–210° C.; Found C 70.45 H 4.60 N 10.99 $C_{22}H_{17}N_3O_3$. 0.25 $CH_3OH$ Requires C 70.45 H 4.47 N 11.08 $v_{max}(cm^{-1})$ 3445.99, 3318.55, 2922.99, 1689.79, 1666.36; $\delta_H$ 3.86 (3H, s, $OCH_3$), 7.02–7.06 (2H, d), 7.50–7.65 (4H, m), 7.72–7.82 (3H, m), 7.88–7.92 (2H, d), 8.08 (1H, s, CONH), 8.10–8.14 (1H, d), 9.1–9.2 (1H, br s, CONH); m/z (EI) 371 (M+), 105.

FURTHER EXAMPLES

The following further examples, and also some of the examples already described, make use of certain common standard procedures. These comprise:

(1) Reaction of Methyl 2,3-diaminobenzoate with Aryl Acid Chlorides (Standard Procedure A)

(2) Benzimidazole Ring Formation by Acid Catalysed Cyclisation (Standard Procedure B)

(3) Amide Formation by Reaction with Liquid Ammonia (Standard Procedure C)

The experimental details of these standard procedures are described below:

Standard Procedure A

An ice/salt bath cooled solution of methyl 2,3-diaminobenzoate (1 equivalent), dry triethylamine (1–1.5 equivalents) and dimethylaminopyridine (DMAP–5 mol %) in half the required volume of dry tetrahydrofuran (THF) was prepared. The required acid chloride (1 equivalent) was dissolved in the remaining dry tetrahydrofuran (THF) and added to the cooled solution with stirring over 30 minutes. The reaction was allowed to warm slowly to room temperature and was stirred overnight. The solvent was filtered to remove a precipitate which was suspended in ethyl acetate, washed twice with water followed by saturated brine, and dried with $MgSO_4$. The organic layer was added to the reaction filtrate, and the solvent removed under reduced pressure. The solid residue was redissolved in ethyl acetate, washed twice with water followed by saturated brine, and dried with $MgSO_4$. Removal of the solvents under reduced pressure left a solid residue which was purified by column chromatography and/or recrystallisation from suitable solvents.

Standard Procedure B

The starting material was dissolved in glacial acetic acid and plunged into a pre-heated oil bath at 120° C. The solution was heated for the appropriate time and then allowed to cool to room temperature. The acetic acid was removed under reduced pressure and the solid residue purified by column chromatography and/or recrystallisation from suitable solvents.

Standard Procedure C

The starting material was dissolved in a excess of freshly condensed liquid ammonia. This was heated to 80° C. within a sealed vessel, generating a pressure of 40 atmospheres, for 24 hours. The ammonia was evaporated, and the solid residue obtained purified by column chromatography and/or recrystallisation from suitable solvents.

EXAMPLE 10

2-(4'-Cyanophenyl)-1-H-benzimidazole-4-carboxamide (NU1092)

(a) 1st Stage—Preparation of Methyl 2-amino-3-N-(4'-cyanobenzoyl)aminobenzoate

Following standard procedure A, methyl 2,3-diaminobenzoate (300 mg, 1.81 mmol), triethylamine (251 μl, 1.81 mmol) and DMAP (11 mg) were dissolved in THF (7.5 ml) and cooled. To this was added 4-cyanobenzoyl chloride (299 mg, 1.81 mmol) dissolved in THF (7.5 ml). The product was purified by column chromatography, dichloromethane/methanol 99:1, followed by recrystallisation from boiling methanol. (196 mg, 37%) mp 198–202° C.; $v_{max}((cm^{-1})$ 3486.40, 3374.02, 3245.61, 2231.25, 1688.04, 1646.65; $\delta_H$ 3.93 (3H, s, $CO_2CH_3$), 6.68–6.76 (1H, t), 6.72 (2H, br s, $NH_2$), 7.45–7.49 (1H, d), 7.81–7.86 (1H, d), 8.11–8.15 (2H, d, J=8.4), 8.25–8.29 (2H, d, J=8.4), 10.01 (1H, br s, NH); m/z (EI) 295 (M+), 278, 263, 246, 130, 102.

(b) 2nd Stage—Preparation of Methyl 2-(4'-cyanophenyl)-1-H-benzimidazole-4-carboxylate Following standard procedure B, methyl 2-amino-3-N-(4'-cyanobenzoyl)aminobenzoate (301 mg, 1.02 mmol) from 1st stage was heated in glacial acetic acid (10 ml). The product was obtained by recrystallising twice using petrol 40/60/ethyl acetate. (203 mg, 72%) mp 195–198° C.; $v_{max}$ $(cm^{-1})$ 3447.66, 2228.84, 1691.90, 1288.11 $\delta_H$ 4.09 (3H, s, $CO_2CH_3$), 7.44–7.53 (1H, t), 7.97–8.01 (1H, d), 8.10–8.13 (2H, d, J=8.4), 8.58–8.62 (2H, d, J=8.4), 12.8 (1H, br s); m/z (EI) 277 (M+), 245, 217

(c) 3rd Stage—Preparation of 2-(4'-Cyanophenyl)-1-H-benzimidazole-4-carboxamide (NU1092)

Following standard procedure C, methyl 2-(4'-cyanophenyl)-1-H-benzimidazole-4-carboxylate (169.5 mg, 0.612 mmol) was treated with ammonia under pressure. The crude product was recrystallised from boiling methanol to yield the title compound pure as white crystals. (116.5 mg, 73%) mp >310° C.; Found C 67.81 H 3.89 N 20.87, $C_{15}H_{10}N4O.0.2$ MeOH Requires C 67.95 H 4.05 N 20.85; $v_{max}(cm^{-1})$ 3332.27, 3274.86, 3177.98, 2230.85, 1658.54, 1608.10; $\delta_H$ 7.45–7.49 (1H, t); 7.87–7.91 (1H, d), 7.91 (1H, br s), 7.98–8.02 (1H, d); 8.13–8.17 (2H, d, J=8.3), 8.50–8.54 (2H, d, J=8.3), 9.2–9.4 (1H, br s), 13.6–13.8 (1H, br 8); m/z (EI) 262 (M+), 245, 217, 102.

EXAMPLE 11

2-(4'-Nitrophenyl)-1-H-benzimidazole-4-carboxamide (NU1091)

(a) 1st Stage—Preparation of Methyl 2-amino-3-N-(4'-nitrobenzoyl)aminobenzoate

Following standard procedure A, methyl 2,3-diaminobenzoate (300 mg, 1.807 mmol), dry triethylamine (276.6 μl, 1.988 mmol) and DMAP (11 mg) were dissolved in dry THF (12 ml). To this was added 4-nitrobenzoyl chloride (335.2 mg, 1.807 mmol) in dry THF (12 ml). Column chromatography with dischloromethane/methanol 99:1 followed by recrystallisation from methanol gave the product pure. mp 196–197° C.; Found C 57.08 H 3.78 N 13.25 $C_{15}H_{13}N_3O_5$ Requires C 57.14 H 4.12 N 13.33; $v_{max}(cm^{-1})$ 3382.31, 3293.01, 3256.56, 1702.05, 1657.83, 1525.37; $\delta_H$ 3.94 (3H, s, $CO_2CH_3$), 6.70–6.78 (1H, t), 6.66 (2H, br s, $NH_2$), 7.48–7.51 (1H, d), 7.83–7.87 (1H, d), 8.33–8.38 (2H, d, J=8.8), 8.46–8.51 (2H, d, J=8.8), 10.15 (1H, br s, NH); m/z (EI) 315 (M+), 297, 265, 165.

(b) 2nd Stage—Preparation of Methyl 2-(4'-Nitrophenyl)-1-H-benzimidazole-4-carboxylate Following standard procedure B, methyl 2-amino-3-N-(4'-nitrobenzoyl)aminobenzoate (340.2 mg, 1.08 mmol) was heated in glacial acetic acid (10 ml) for 15 minutes. The product was obtained pure by recrystallisation from methanol. (208 mg, 65%). mp 208–210° C.; Found C 60.69 H 3.57 N 13.96 $C_{15}H_{11}N_3O_4$ Requires 60.61 H 3.70 N 14.14; $v_{max}(cm^{-1})$ 3433.70, 1720.14, 1601.84, 1513.07; $\delta_H$ 4.21 (3H, s, $CO_2CH_3$), 7.57–7.65 (1H, t), 8.10–8.12 (1H, d), 8.23–8.27 (1H, d), 8.60–8.64 (2H, d, J=8.8), 8.78–8.82 (2H, d, J=8.8), 13.04 (1H, br s, NH); m/z (EI) 297 (M+), 265.

(c) 3rd Stage—Preparation of 2-(4'-Nitrophenyl)-1-H-benzimidazole-4-carboxamide (NU1091)

Following standard procedure C, methyl 2-(4'-nitrophenyl)-1-H-benzimidazole-4-carboxylate was dissolved in liquid ammonia and heated under constant volume in a pressure vessel. The product was purified by column chromatography from dichloromethane/methanol 99:1 and recrystallised from methanol. mp >310° C.; $\delta_H$ 7.48–7.56 (1H, t), 7.90–7.94 (1H, d), 8.00 (1H, s, NH), 8.00–8.04 (1H, d), 8.52–8.56 (2H, d, J=8.8), 8.60–8.64 (2H, d, J=8.8), 9.3–9.4 (1H, br s, NH), 13.8–14.0 (1H, br s, NH)

EXAMPLE 12

2-(3'-Trifluoromethylphenyl)-1-H-benzimidazole-4-carboxamide (NU1093)

(a) 1st Stage—Preparation of Methyl 2-amino-3-N-(3'-trifluoromethylbenzoyl)aminobenzoate Following standard procedure A, methyl 2,3-diaminobenzoate (200 mg, 1.205 mmol), dry triethylamine (704 μl, 5.06 mmol) and dimethylaminopyridine (DMAP, 7.3 mg) were dissolved in dry THF (7.5 ml). To this was added 3-trifluoromethylbenzoyl chloride (183 μl, 1.205 mmol) in dry THF (7.5 ml). Column chromatography with dichloromethane/methanol 99:1 removed impurities and the more polar product was eluted with dichloromethane/methanol 97:3. Recrystallisation from methanol gave the product as a white solid. (160.4 mg, 26%). mp 157–159° C.; Found C 57.14 H 3.57 N 8.10 $C_{16}H_{13}F_3N_2O_3$ Requires C 56.80 H 3.85 N 8.28; $v_{max}(cm^{-1})$ 3368.48, 3283.82, 2953.87, 1705.98, 1650.77, 1250.02; $\delta_H$ 3.93 (3H, s, $CO_2CH_3$), 6.69–6.77 (1H, t), 6.73 (2H, s, $NH_2$), 7.45–7.49 (1H, d), 7.82–7.92 (2H, m), 8.06–8.10 (1H, d), 8.40–8.44 (1H, d), 8.48 (1H, s, 2'-H), 10.1 (1H, s, NH); m/z (EI) 338 ($M^+$), 320, 288, 260, 173, 145.

(b) 2nd Stage—Preparation of Methyl 2-(3'-trifluoromethylphenyl)-1-H-benzimidazole-4-carboxylate Acetate Salt Following standard procedure B, a glacial acetic acid (6 ml) solution of methyl 2-amino-3-N-(3'-trifluoromethylbenzoyl)aminobenzoate was heated for 15 minutes. Removal of the solvent under reduced pressure followed by drying at high vacuum yielded the product as a pure white solid. (154.2 mg, 96%). mp 105–107° C.; Found C 56.93 H 3.78 N 7.32 $C_{16}H_{11}F_3N_2O_2.CH_3CO_2H$ Requires C 56.84 H 3.95 N 7.37 $v_{max}(cm^{-1})$ 3438.30, 3339.14, 2959.13, 1707.99, 1328.24, 1313.53; $\delta_H$ 2.01 (3H, s, $CH_3CO_2H$), 4.09 (3H, s, $CO_2CH_3$), 7.44–7.51 (1H, t), 7.79–8.13 (4H, m), 8.71–8.75 (1H, d), 8.82 (1H, s), 11.8–12.2 (1H, br s), 12.8–13.0 (1H, br s); m/z (EI) 320 ($M^+$—$CH_3CO_2H$), 288, 260.

(c) 3rd Stage—Preparation of 2-(3'-trifluoromethyl phenyl)-1-H-benzimidazole-4-carboxamide (Compound NU1093)

Following standard procedure C, the acetate salt of methyl 2-(3'-trifluoromethylphenyl)-1-H-benzimidazole-4-carboxylate (134.8 mg, 0.358 mmol) was treated with excess liquid ammonia in a sealed vessel. The product was purified by recrystallisation from methanol, to yield off-white needles. (78 mg, 72%). mp 268–270° C.; Found C 57.68 H 3.82 N 12.96 $C_{15}H_{10}F_3N_3O.0.6CH_3OH$ Requires C 57.74 H 3.82 N 12.95; $v_{max}(cm^{-1})$ 3488.83, 3348.86, 3176.45, 1667.66, 1600.93, 1329.63; $\delta_H$ 7.44–7.52 (1H, t), 7.88–8.04 (5H, m), 8.66–8.70 (1H, d), 8.70 (1H, s, 2' H), 9.3 (1H, br s, NH), 13.6 (1H, br s, NH); m/z (EI) 305 ($M^+$), 288, 260, 145.

EXAMPLE 13

2-(3'-Methoxyphenyl)-1-H-benzimidazole-4-carboxamide (NU 1098)

(a) 1st Stage—Preparation of Methyl 2-amino-3-N-(3'-methoxybenzoyl)aminobenzoate Following standard procedure A, a solution of methyl 2,3-diaminobenzoate (670.3 mg, 4.038 mmol), dry triethylamine (842.6 μl, 6.057 mmol) and DMAP (25 mg) in dry THF (20 ml) was prepared. A solution of 3-methoxybenzoyl chloride (567 μl, 6.038 mmol) in dry THF (20 ml) was added to this. The resulting solid residue was purified by column chromatography using dichloromethane/methanol 99:1 and the product was obtained pure after two recrystallisations from petrol 40/60/ethyl acetate. (282.6 mg, 23%) mp 124–125° C.; Found C 63.90 H 5.11 N 9.24 $C_{16}H_{16}N_2O_4$ Requires C 64.0 H 5.33 N 9.33; $v_{max}(cm^{-1})$ 3386.19, 3292.38, 1697.97, 1586.87, 1520.79, 1250.27; $\delta_H$ 3.92 (3H, s), 3.93 (3H, s), 6.61 (2H, s, $NH_2$), 6.68–6.76 (1H, t), 7.22–7.27 (1H, d), 7.44–7.47 (1H, d), 7.49–7.57 (1H, t), 7.66 (1H, s, 2'-H), 7367–7.71 (1H, d), 7.79–7.84 (1H, d), 9.8 (1H, s, NH); m/z (EI) 300 ($M^+$), 283, 135, 107.

(b) 2nd Stage—Preparation of Methyl 2-(3'-methoxyphenyl)-1-H-benzimidazole-4-carboxylate Acetate Salt Following standard procedure B, methyl 2-amino-3-N-(3'-methoxybenzoyl)aminobenzoate (356.9 mg, 1.19 mmol) was warmed in glacial acetic acid (12 ml. The removal of the solvent under reduced pressure followed by recrystallisation with petrol 40/60/ethyl acetate afforded the title compound pure. (235.6 mg, 58%) mp 93–94° C.; Found C 62.66 H 5.13 N 8.06 $C_{16}H_{14}N_2O_3.CH_3CO_2H$ Requires C 63.16 H 5.26 N 8.18 $v_{max}(cm^{-1})$ 3453.23, 3375.10, 1706.75, 1257.40; $\delta_H$ 1.99 (3H, s, $CH_3CO_2H$), 3.96 (3H, s), 4.06 (3H, s), 7.15–7.21 (1H, d), 7.38–7.46 (1H, t), 7.51–7.59 (1H, t), 7.91–8.00 (3H, m), 8.04–8.08 (1H, d), 12.0 (1H, s), 12.5 (11H, s); m/z (EI) 282 ($M^+$—$CH_3CO_2H$), 250.

(c) 3rd Stage—Preparation of 2-(3'-Methoxyphenyl)-1-H-benzimidazole-4-carboxamide (NU1098)

Following standard procedure C, a liquid ammonia solution of methyl 2-(3'-methoxyphenyl)-1-H-benzimidazole-4-carboxylate (203 mg, 0.596 mmol) was heated under constant volume. The solid residue was recrystallised from methanol to give the pure product (73.5 mg, 46%). mp 223–225° C.; Found C 67.52 H 4.91 N 15.62 $C_{15}H_{13}N_3O_2$ Requires C 67.42 H 4.87 N 15.73; $v_{max}(cm^{-1})$ 3408.59, 3388.94, 3168.65, 1662.05, 1625.86, 1603.39; $\delta_H$ 3.99 (3H, s, $OCH_3$), 7.22–7.27 (1H, d),7.43–7.51 (1H, t), 7.58–7.66 (1H, t), 7.85–8.01 (5H, m), 9.4–9.5 (1H, br s), 13.5 (1H, br s); m/z (EI) 267 ($M^+$), 250.

EXAMPLE 14

2-(2'-trifluoromethylphenyl)-1-H-benzimidazole-4-carboxamide (NU1104)

(a) 1st Stage—Preparation of Methyl 2-amino-3-N-(2'-trifluoromethylbenzoyl)aminobenzoate Following standard procedure A, methyl 2,3-diaminobenzoate (564 mg, 3.4 mmol) in a THF (20 ml) solution with triethylamine (709 μl, 5.1 mmol) and dimethylaminopyridine (21 mg) was stirred and to this was added a THF (20 ml) solution of 2-trifluoromethylbenzoyl chloride. The resulting oily residue was absorbed onto silica and then subjected to column chromatography with dichloromethane/methanol 99:1 as eluant. The product was obtained pure after recrystallisation from petrol 40/60/ethyl acetate. (303 mg, 26%). mp 163–166° C.; Found C 56.91 H 3.75 N 8.29 $C_{16}H_{13}F_3N_2O_3$ Requires C 56.80 H 3.85 N 8.28; $v_{max}(cm^{-1})$ 3329.85, 3243.90, 2955.52, 1696.66, 1663.58, 1312.69; $\delta_H$ 3.94 (3H, s, $CO_2CH_3$), 6.58 (2H, s, $NH_2$), 6.74–6.82 (1H, t), 7.57–7.62 (1H, d), 7.79–8.03 (5H, m), 10.0 (1H, s, NH); m/z (EI) 338 ($M^+$), 321, 289, 173, 145.

(b) 2nd and 3rd Stages—Preparation of 2-(2'-trifluoromethyl)-1-H-benzimidazole-4-carboxamide (NU1104)

Upon subjecting the product of the 1st stages successively to standard procedures B and C, the title compound was obtained.

EXAMPLE 15

2-(4'-Aminophenyl)-1-H-benzimidazole-4-carboxamide (NU1103)

(a) 1st Stage—Preparation of Methyl-2-amino-3-N-(4'-aminobenzoyl)aminobenzoate

Methyl-2-amino-3-N-(4'-nitrobenzoyl)aminobenzoate (from 1st stage of Example 11) was suspended in methanol (40 ml) and a slurry of 10% palladium catalyst on activated carbon (~50 mg) in methanol (10 ml) was added to this with stirring under argon. The solution was atmospherically hydrogenated for 2 hours. After filtration through CELITE (Regd.™) to remove the catalyst the product was obtained by removal of the solvent under reduced pressure to give a white solid which was dried under high vacuum. (204.1 mg, 92%). mp 197–200° C.; Found C 62.95 H 5.30 N 14.39 $C_{15}H_{15}N_3O_3$ Requires C 63.16 H 5.26 N 14.73; $v_{max}(cm^{-1})$ 3472.55, 3374.96, 3348.97, 3283.31, 1694.80, 1613.91; $\delta_H$ 3.94 (3H, s, $CO_2CH_3$), 5.87 (2H, s, $NH_2$), 6.54 (2H, s, $NH_2$), 6.68–3.73 (2H, d), 6.73–6.76 (1H, t), 7.42–7.47 (1H, d), 7.78–7.82 (2H, d), 9.4 (1H, s, NH); m/z (EI) 285 ($M^+$), 267, 235, 207, 120, 92.

(b) 2nd Stage—Preparation of Methyl 2-(4'-aminophenyl)-1-H-benzimidazole-4-carboxylate Acetate Salt Following standard procedure B, the treatment of methyl 2-amino-3-N-(4'-aminobenzoyl)aminobenzoate (186.5 mg, 0.654 mmol) with hot glacial acetic acid (8 ml) for 30 minutes yielded the title compound following recrystallisation from petrol 40/60/ethyl acetate. (113.4 mg, 91%) mp 162–164° C.; Found C 62.60 H 5.04 N 12.73 $C_{15}H_{13}N_3O_2 \cdot CH_3CO_2H$ Requires C 62.39 H 5.20 N 12.84; $v_{max}(cm^{-1})$ 3450.66, 3369.25, 3254.20, 1692.41, 1607.56, 1253.80; $\delta_H$ 2.02 (3H, s, $CH_3CO_2H$), 4.08 (3H, s, $CO_2CH_3$), 5.81 (2H, s, $NH_2$), 6.75–6.80 (2H, d, J=8.6), 7.32–7.40 (1H, t), 7.83–7.86 (1H, d), 7.93–7.97 (1H, d), 8.08–8.13 (2H, d, J=8.6), 11.9 (1H, s), 12.1 (1H, br s); m/z (EI) 267 ($M^+$—$CH_3CO_2H$), 235, 207, 92, 60.

(c) 3rd Stage—Preparation of 2-(4'-Aminophenyl)-1-H-benzimidazole-4-carboxamide (NU1103)

Following standard procedure C, the acetate salt of methyl 2-(4'-aminophenyl)-1-H-benzimidazole-4-carboxylate (113 mg, 0.346 mmol) was treated with liquid ammonia under pressure for 24 hours. The pure title compound was isolated with column chromatography of the crude material using dichloromethane/methanol 90:10 (21.4 mg, 25%) mp 237–240° C.; $\delta_H$ 5.90 (2H, s, $NH_2$), 6.79–6.83 (2H, d, J=8.3), 7.31–7.39 (1H, t), 7.71–7.75 (1H, d), 7.84 (1H, s, NH), 7.88–7.92 (1H, d), 8.00–8.04 (2H, d, J=8.3), 9.5–9.6 (1H, br s, NH), 13.0 (1H, br s, NH).

ASSAY FOR PARP INHIBITORY ACTIVITY

Compounds of the present invention, particularly those detailed in the preceding Examples, have been tested in vitro for activity as PARP inhibitors using the following methods and materials.

In principle, the PARP assay used relies upon activating endogenous PARP (as hereinafter described) in cells containing exogenous [$^{32}$P]-NAD$^+$ introduced therein by suspending the cells in a solution of [$^{32}$P]-NAD$^+$ to which they have been rendered permeable in an initial pre-treatment step. The poly(ADP-ribose) which is then synthesised by the enzyme can be precipitated by trichloracetic acid (TCA) and the amount of radio-labelled $^{32}$P incorporated therein measured, e.g. using a scintillation counter, to give a measure of the activity of the PARP under the particular conditions of the experiment. By repeating the experiment following the same procedure, and under the same conditions, in the presence of each compound to be tested the reduction in enzyme activity, representative of the inhibitory effect of the test compound, can then be ascertained from the reduction, if any, of the amount of [$^{32}$P] measured in the TCA precipitated poly(ADP-ribose).

The results of this assay may be expressed in terms of percentage inhibition or reduction in activity for one or more different concentrations of each compound tested, or it may be expressed in terms of that concentration of the tested compound which reduces the enzyme activity by 50%, i.e. the $IC_{50}$ value. Thus, with a range of different compounds a set of comparative values for inhibitory activity can be obtained.

In practice, L1210 murine leukemia cells have been used as a source of the PARP enzyme after being rendered permeable to exogenous [$^{32}$P] NAD by exposure to hypotonic buffer and cold shock. In the preferred technique which has been found to give exact and reproducible results, a defined amount of a small synthetic oligonucleotide, in particular a single strand oligonucleotide having the palindromic sequence CGGAATTCCG, is introduced into the cell suspension for activating the PARP enzyme. This oligonucleotide sequence snaps back on itself to form a double-stranded molecule with a single blunt end and provides an effective substrate for activation of PARP. Its behavior as a potent activator of the enzyme was confirmed in the tests carried out.

The experimental protocol adopted, in which a synthetic oligonucleotide as mentioned above is introduced as a specific activator of PARP, discriminates between PARP and other mono-ADP-ribosyltransferases in the cells. Thus, introduction of such synthetic oligonucleotides causes a 5 to 6 fold stimulation in the radioactive label incorporated and this is attributable solely to PARP activity.

Further details of the assay are given below.

Materials

The materials used included the following:

DTT (Dithiothreitol)

A 100 mM (15.4 mg/ml) solution (for use as an antioxidant) was made up, divided into 500 µl aliquots and stored at −20° C.

Hypotonic Buffer

| 9 mM Hepes | (214 mg/100 ml) |
| 4.5% Dextran | (4.5 g/100 ml) |
| 4.5 mM $MgCl_2$ | (92 mg/100 ml) |

The above ingredients were dissolved in about 80 ml distilled water, pH was adjusted to 7.8 (NaOH/HCl), the solution was then made up to 100 ml with distilled water, and stored in a refrigerator.

DTT was added to 5 mM just before use (50 µl/ml).

Isotonic Buffer

| 40 mM Hepes | (1.9 g/200 ml) |
| 130 mM KCl | (1.94 g/200 ml) |
| 4% Dextran | (8 g/200 ml) |
| 2 mM EGTA | (152 mg/200 ml) |

-continued

| 2.3 mM MgCl$_2$ | (94 mg/200 ml) |
| 225 mM Sucrose | (15.39 g/200 ml) |

The above ingredients were dissolved in about 150 ml distilled water, pH was adjusted to 7.8 (NaOH/HCl), the solution was then made up to 200 ml with distilled water and stored in a refrigerator. DTT was added to 2.5mM just before use (25µl/ml).

NAD

NAD was stored as a solid in pre-weighed aliquots at −20° C. From these, solutions of a concentration of approximately 6mM (4–4.5 mg/ml) were freshly made up shortly before performing an assay, and the molarity was checked by measuring the optical density (O.D.) at 260 nm. The stock solution was then diluted with water to give a concentration of 600µM and a small amount of $^{32}$P labelled NAD was added (e.g. 2–5 µl/ml).

Oligonucleotide

The oligonucleotide having the palindromic sequence CGGAATTCCG, synthesised by conventional means, was vacuum dried and stored as pellets in a freezer. Before use, it was made up to 200 µg/ml in 10 mM Tris/HCl, pH 7.8, with each pellet being dissolved completely in 50 ml of buffer. The solution was then heated to 60° C. in a water bath for is minutes, and allowed to cool slowly to ensure correct reannealing. After adding 9.5 ml of buffer, the concentration was checked by measuring the optical density of a diluted sample at 260 nm.

The main solution was then diluted to a concentration of 200 µg/ml and stored in 500 µl aliquots in a freezer, ready for use.

TCA

Solutions of TCA (Trichloroacetic acid) were prepared at two concentrations. 10% TCA+10% sodium pyrophosphate, and 1% TCA+1% sodium pyrophosphate.

Cells

The L1210 cells used as the source of the PARP enzyme were maintained as a suspension culture in RPMI medium+10% foetal bovine serum+glutamine and antibiotics (penicillin and streptomycin). HEPES and sodium bicarbonate were also added, and the cells were seeded in 100 ml–200 ml of medium such that there would be a concentration of approximately 8×10$^5$/ml at the time of carrying out an assay.

Method

The compounds being tested were generally made up as a concentrated solution in DMSO (Dimethyl sulphoxide). The solubility of the compound was then checked by adding a quantity of the DMSO solution to a quantity of the isotonic buffer, in the required final proportions that were to be used in carrying out the assay, and after an interval the solution was examined under a microscope for any signs of crystals forming.

A desired quantity of the cells, ascertained by counting with a haemocytometer, was then centrifuged (1500 rpm in a "Europa" model 24M centrifuge for 5 minutes), the supernatant removed, and the pellets obtained were resuspended in 20 ml Ca$^{++}$ Mg$^{++}$ free phosphate buffered saline (Dulbeco's modification A, abbreviated Dul A). at 4° C. before centrifuging again at 1500 rpm and 4° C. After again removing the supernatant, the cells were resuspended at a concentration of 3×10$^7$ cells/ml in ice cold hypotonic buffer and left for 30 minutes on ice. Nine volumes were then added of ice cold isotonic buffer, and the cells, now rendered permeable to exogenous NAD$^+$, were then used within the next hour for carrying out an assay. The permeablisation of the cells may be checked at this stage by adding duplicate aliquots of cells to an equal volume of trypan blue, leaving for 5 minutes and then counting on a haemocytometer. Those rendered permeable will take up the Trypan blue and appear coloured.

The assay was then carried out using for convenience plastic 15 ml conical bottomed assay tubes set up in a shaking water bath at 26° C. which is the optimum temperature for this enzyme. In a typical assay using the oligonucleotide solution at a concentration of 5 µg/ml and the test compound/DMSO solution at a concentration of 2%, and carrying out the assay in quadruplicate, there would then be placed in each assay tube 5 µl of the oligonucleotide solution, 50 µl of the 600 µm NAD+[$^{32}$P]-NAD solution, 8 µl of the test compound/DMSO solution, and 37 µl of water. Prior to the start of the experiment this "cocktail" would be pre-warmed for 7 minutes at 26° C., as would be also the cell suspension. The reaction would then be started by adding 300 µl of the cell suspension. The reaction would be stopped by adding 2 ml of the ice-cold 10% TCA+10% sodium pyrophosphate solution.

In addition to the above, six assay tubes would usually be set up as blanks, these containing the same ingredients as above but, before adding the cell suspension, TCA solution is added to prevent any reaction from taking place. This enables corrections to be applied for any non-specific binding of the labelled material to the filter used (see below).

After adding the cell suspension at timed intervals to each of the assay tubes, the 10% TCA+10% sodium pyrophosphate at 4° C. was added to each assay tube exactly 5 minutes after addition of the cell suspension to that tube. Then, after leaving the tubes on ice for a minimum time of one hour, the contents of each individual tube were filtered through an individual filter funnel of a suction filter apparatus using GF/C filter elements (rough side up) wetted with 10% TCA. After filtering the contents of each tube and rinsing the filters several times with 1% TCA+1% sodium pyrophosphate solution, the filters were carefully removed and dried before being placed in individual scintillation vials. Four additional scintillation vials were also set up as reference standards containing 10 µl of the 600 µM NAD+ [$^{32}$P]-NAD solution, 10 ml scintillant then being added to each vial. Counting was carried out for 2 minutes on a β counter to obtain measures of the $^{32}$P present, and thus the amount of the poly(ADP-ribose) and activity of the PARP enzyme.

RESULTS OF IN VITRO PARP INHIBITION STUDIES

Apart from applying the PARP enzyme assay in accordance with the standard procedure outlined above to a range of compounds which have been made in accordance with the present invention, for comparison purposes it was also applied to certain benzamide compounds, in particular benzamide, 3-hydroxybenzamide and 3-methoxybenzamide, that are already known to exhibit certain PARP inhibitory activity. A tabulated list of some exemplary compounds which have been made and/or studied is hereinafter presented in the TABLE at the end of the present description, together with the PARP inhibition assay results obtained in one or more different experiments, expressed either as the percentage inhibition at a 10 µM concentration or, more usually, as $IC_{50}$ values, for the compounds when tested using the assay hereinabove described.

In reviewing this list, the known PARP inhibitors benzamide, 3-aminobenzamide and 3-methoxybenzamide, may be regarded as reference compounds. Although the results varied somewhat, in general the compounds of the present invention which were tested showed a relatively high degree of inhibitory activity. Of especial interest were the benzimidazole carboxamides having the reference numbers NU1064, NU1066, NU1086 and, most particularly, NU1070, NU1076, NU1077, NU1085, NU1090, NU1091, NU1092, NU1093 and NU1098, of which NU1091 and NU1092 showed exceptionally high inhibitory activities.

FURTHER BIOLOGICAL ACTIVITY STUDIES

Again using cultures of the murine leukaemia L1210 cell line, growth inhibition experiments were carried out to assess the cytostatic effects of the compounds and clonogenic survival assays were performed to assess cytotoxicity, especially in relation to use of the compounds in conjunction with DNA damaging cytotoxic agents such as cytotoxic antitumour drugs or gamma irradiation. DNA damage and the effect of the PARP inhibitors on the process of DNA strand break formation and repair has also been assessed by carrying out DNA strand break assays and monitoring by alkaline elution in accordance with published techniques.

In the growth inhibition assays, typically the L1210 cells would be seeded at $1 \times 10^4$/ml in triplicate in 24 well multidishes, and 24 hours later the compounds or drugs being tested would be added in selected combinations and concentrations. At this time one set of replicates would be counted using a Coulter counter ($N_0$), and 48 hours later the remaining samples would be counted ($N_1$). The percentage (%) growth inhibition of drug-treated samples could then be estimated. In drug combination experiments, where evidence of synergistic effects on cell growth or clonogenicity was being sought, a single, fixed concentration of a cytotoxic drug sample, e.g. temozolomide (TM), would be taken as the control value.

Examples of in vitro Cytotoxicity Assays

In a particular example of an in vitro cytotoxicity assay using the compound NU1064 (2-methylbenzimidazole-4-carboxamide), L1210 murine leukaemia cells were incubated with increasing concentrations of NU1064 in the presence or absence of 100 $\mu$M of the methylating agent, temozolomide, in a final DMSO concentration of 1% DMSO, for 24 hours at 36° C. The cells were pelleted, resuspended in fresh medium, counted and seeded for colony formation in 0.15% agarose in drug-free medium. After 1 week colonies of viable cells were stained with MTT (1 ml 0.5 mg/ml) and counted. The plating efficiency of the control (89%) and temozolomide alone (32%) were normalised to 100% relative survival and the plating efficiency of the NU1064-treated cells expressed as a percentage of these values.

There was a modest reduction in cell survival caused by NU1064 alone (relative plating efficiency at 100 $\mu$M and 200 $\mu$M NU1064=72% and 54%, respectively) but a very marked increase in temozolomide cytotoxicity with increasing concentrations of NU1064 (relative plating efficiency at 100 and 200 $\mu$M NU1064=28% and 2%, respectively) indicating a NU1064-concentration-related potentiation of temozolomide cytotoxicity. An illustration of these results is presented by FIG. 1 of the accompanying drawing.

In other, clonogenic survival, assays, typically the L1210 cells would be exposed to varying concentrations of TM±a fixed concentration of PARP inhibitor for a fixed time of 16 hours, prior to counting and seeding for colony formation in 0.12–0.15% agarose in drug-free medium. After 7–10 days colonies would be stained with 0.5 mg/ml MTT and counted by eye on a gridded light box. This then enables survival curves to be plotted and $DEF_{10}$ values to be obtained, $DEF_{10}$ being defined as the ratio of the concentration of TM that reduces survival to 10% divided by the concentration of TM that reduces survival to 10% in the presence of a fixed concentration of PARP inhibitor.

In further clonogenic survival assays gamma ray irradiation may be used to damage the cells. Typically, L1210 cells (3 ml, $4 \times 10^3$/ml in plastic bijoux bottles) would be irradiated at 4° C. with varying doses of gamma rays in the presence or absence of the compound being tested and a final concentration of 2% DMSO. The cells would then be incubated at 37° C. for 2 hours in the continued presence or absence of PARP inhibitor prior to seeding for colony formation.

Repair of potentially lethal damage (PLD) occurs when cells are held in stationary-phase following initiation of PLD prior to allowing cell division to take place. In further typical experiments to test potential PARP inhibitors, L1210 cells have been allowed to repair gamma ray PLD in the presence or absence of the test compound as follows: L1210 cells were maintained in culture until they had attained stationary phase ($>10^6$cells/ml). They were diluted to $1.5 \times 10^5$/ml in conditioned medium from stationary-phase cultures to prevent further cell division. Replicate 2 ml samples of cells in plastic bijoux were held on ice prior to and immediately following 8 Gray gamma ray irradiation. 1 ml of 3× final concentration of the test compounds made up in conditioned medium from stationary cultures would then be added to give appropriate final concentrations (e.g. $10^6$cells/ml in 1% DMSO±test compounds), and the cells would be incubated at 37° C. for 0, 2 or 4 hours prior to resuspending in drug-free medium and seeding for colony formation. Unirradiated stationary phase cultures incubated at 37° C. for 0, 2 or 4 hours with 1% DMSO±the same amount of test compound provide appropriate controls for determining relative cell survival. In the absence of PARP inhibitor cell survival would normally increase with time allowed for PLD repair to take place. For example, in one set of experiments, when seeded immediately after irradiation (no repair) only about 0.2% of the cells survived, but after a 4 hour repair period this had increased to 0.7%. An effective PARP inhibitor blocks this repair, thus reducing the survival rate.

With regard to the DNA strand break assays previously mentioned, typically samples of L1210 cells would be incubated for a certain time, e.g. 1 hour, with a fixed concentration, e.g. 150 $\mu$M, of temozolomide and, apart from a control, in the presence of increasing concentrations of the PARP inhibitors tested. The more effective the inhibitor, the greater the rate of the alkaline elution (a measure of extent of strand breakage) compared to temozolomide alone.

In general, the studies carried out fully support the belief that the PARP inhibitory characteristics of the compounds tested reflect an ability of these compounds to potentiate the cytotoxicity of DNA damaging agents, such as certain cytotoxic antitumour drugs and radiation used in radiotherapy. Accordingly, having regard to their strong PARP inhibitory characteristics, the compounds of this invention can be expected to be especially useful for administration in conjunction with such cytotoxic drugs or radiotherapy in order to potentiate the cytotoxic effect of the latter in the course of medical treatment as hereinbefore indicated.

Summary

Although the present invention should be regarded overall as comprising each and every novel feature or combination of features disclosed herein, the main aspects of the invention comprise, principally but not exclusively, broadly the following:

(i) Novel compounds of formula (I) as defined herein;
(ii) Compounds of formula (I) with substituents as hereinbefore defined (including pro-drug forms and salts thereof) for therapy or for use in medicine and in the manufacture of medical preparations, useful for example as PARP inhibitors to be administered in conjunction with cytotoxic drugs or with radiotherapy to potentiate the effectiveness of the latter in treatment of cancer;
(iii) Processes for the preparation of novel compounds of formula (I) as defined herein, including any novel intermediate compounds produced in carrying out such processes;
(iv) Pharmaceutical formulations comprising a compound of formula (I) as defined herein together with a pharmaceutically acceptable carrier therein; and
(v) Processes for the preparation of a pharmaceutical formulation as defined in (iv) above, e.g. by methods referred to herein.

| House No. | Name | Structure | % Inhibition at 10 $\mu$M or IC$_{50}$ value |
|---|---|---|---|
| Ref | benzamide $C_7H_7O$ MW = 121.1 | | IC$_{50}$ = 12.4 ± 3.1 $\mu$M |
| Ref | 3-hydroxybenzamide $C_7H_7NO_2$ MW = 137 | | ID$_{50}$ = 8.0 ± 3.5 $\mu$M (7) |
| Ref | 3-methoxybenzamide $C_8H_9NO_2$ MW = 151 | | 55 |
| NU1064 | 2-methylbenzimidazole-4-carboxamide $C_9H_9N_3O$ MW = 175.38 | 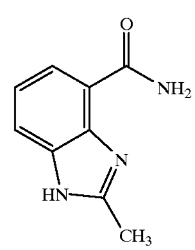 | IC$_{50}$ = 1.09 ± 0.23 $\mu$M (3) |
| NU1066 | benzimidazole-4-carboxamide $C_8H_7N_3O$ MW = 161.16 | 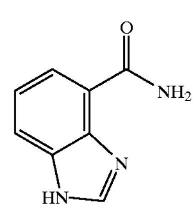 | IC$_{50}$ = 1.26 $\mu$M IC$_{50}$ = 1.02 $\mu$M |

-continued

| House No. | Name | Structure | % Inhibition at 10 μM or IC$_{50}$ value |
|---|---|---|---|
| NU1067 | benzimidazole-4-carboxylic acid<br>C$_8$H$_6$N$_2$O$_2$<br>162.14 | 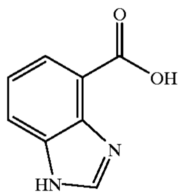 | Inactive |
| NU1070 | 2-phenylbenzimidazole-4-carboxamide<br>C$_{14}$H$_{11}$N$_3$O<br>237.26 | 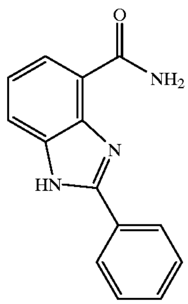 | IC$_{50}$ = 92 nM<br>IC$_{50}$ = 103 nM |
| NU1076 | 2-(4-methoxyphenyl)benzimidazole-4-carboxamide<br>C$_{15}$H$_{13}$N$_3$O$_2$<br>267.28 | 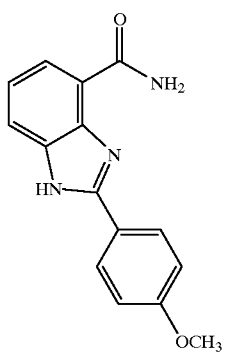 | IC$_{50}$ = 59 nM |
| NU1077 | 2-(4-trifluoromethylphenyl)benzimidazole-4-carboxamide<br>C$_{15}$H$_{10}$N$_3$OF$_3$<br>305.25 | 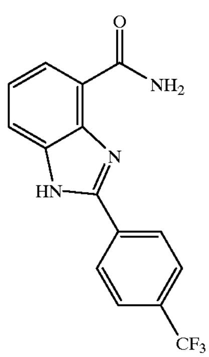 | IC$_{50}$ = 75 nM |
| NU1085 | 2-(4-hydroxyphenyl)benzimidazole-4-carboxamide<br>C$_{14}$H$_{11}$N$_3$O$_2$<br>253.26 | 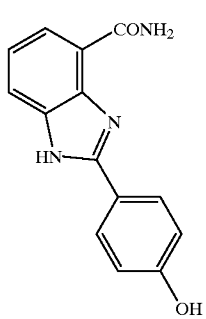 | IC$_{50}$ = 77 nM |

-continued

| House No. | Name | Structure | % Inhibition at 10 μM or IC$_{50}$ value |
|---|---|---|---|
| NU1086 | 2-trifluoromethyl-benzimidazole-4-carboxamide<br>C$_{16}$H$_{15}$N$_3$O$_2$<br>281.31 | 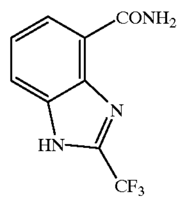 | IC$_{50}$ = 1.6 μM |
| NU1090 | 2-(4-methoxyphenyl)-N-methylbenzimidazole-4-carboxamide<br>C$_{16}$H$_{15}$N$_3$O$_2$<br>281.31 | 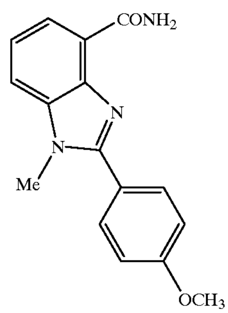 | IC$_{50}$ = ~100 nM |
| NU1091 | 2-(4-nitrophenyl)-benzimidazole-4-carboxamide<br>C$_{14}$H$_{10}$N$_4$O$_3$<br>282.25 | 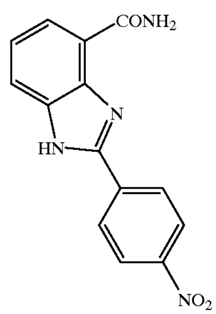 | IC$_{50}$ = 22 nM |
| NU1092 | 2-(4-cyanophenyl)-benzimidazole-4-carboxamide<br>C$_{14}$H$_{10}$N$_4$O<br>262.27 | 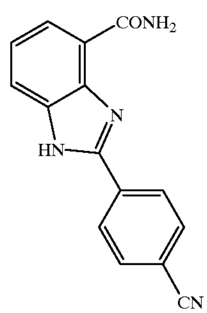 | IC$_{50}$ = 33 nM |
| NU1093 | 2-(3-trifluoromethyl-phenyl)benzimidazole-4-carboxamide<br>C$_{15}$H$_{10}$N$_3$OF$_3$<br>305.25 | 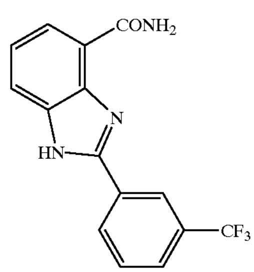 | IC$_{50}$ = 76 nM |

-continued

| House No. | Name | Structure | % Inhibition at 10 μM or IC$_{50}$ value |
|---|---|---|---|
| NU1098 | 2-(3-methoxyphenyl)benzimidazole-4-carboxamide<br>C$_{15}$H$_{13}$N$_3$O$_2$<br>267.28 | 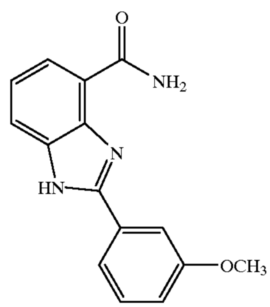 | IC$_{50}$ = 130 nM |
| NU1101 | N-benzoyl-2-(4-methoxyphenyl)-benzimidazole-4-carboxamide<br>C$_{22}$H$_{17}$N$_3$O$_3$<br>371.39 | 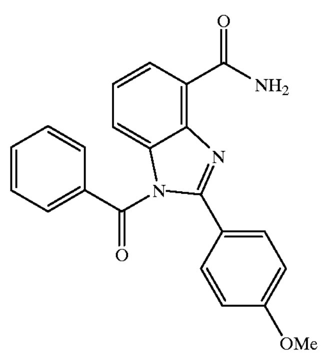 | IC$_{50}$ = 0.27 μM |
| NU1103 | 2-(4-aminophenyl)-benzimidazole-4-carboxamide<br>C$_{14}$H$_{12}$N$_4$O<br>252.27 | 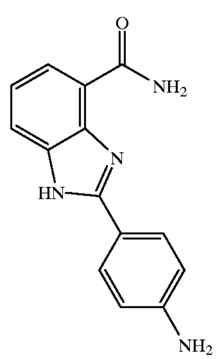 | IC$_{50}$ = 91 nM |
| NU1104 | 2-(2-trifluoromethyl-phenyl)benzimidazole-4-carboxamide<br>C$_{15}$H$_{10}$N$_3$OF$_3$<br>305.25 | 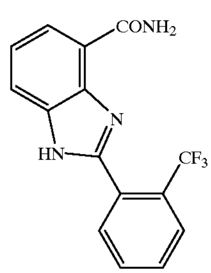 | Not tested |

-continued

| House No. | Name | Structure | % Inhibition at 10 μM or IC$_{50}$ value |
|---|---|---|---|
| NU1105 | N-carboxybenzyl-2-(4-methoxyphenyl)-benzimidazole-4-carboxamide<br>$C_{23}H_{19}N_3O_4$<br>401.42 | 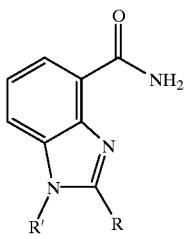 | 1.9 μM |

What is claimed is:

1. A pharmaceutical composition comprising an effective poly(ADP-ribose)polymerase or PARP enzyme inhibiting amount of a benzimidazole compound having the structural formula I

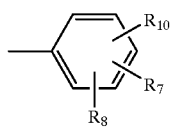

I or a pharmaceutically acceptable salt and/or pro-drug form thereof, together with a pharmaceutically acceptable carrier, wherein R is selected from the group consisting of hydrogen, hydroxyalkyl and a phenyl group which is substituted with one or more substituents selected from the group consisting of $NO_2$, $N_3$, $NHCOR_3$ ($R_3$ being alkyl or aryl), $CO_2R_4$ ($R_4$ being H or alkyl), an amide, tetrazole, alkyl, hydroxyalkyl, $CW_3$ or W (W being halogen), and CN, and R' is selected from the group consisting of hydrogen, alkyl, hydroxyalkyl, acyl and an optionally substituted phenyl group having the structural formula III:

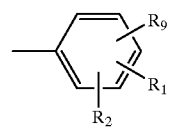

III wherein $R_7$, $R_8$ and $R_{10}$ are each selected independently from the group consisting of H, hydroxy, alkoxy, $NO_2$, $N_3$, $NR_5R_6$ ($R_5$ and $R_6$ each being independently hydrogen, alkyl or alkoxy), $NHCOR_3$ ($R_3$ being alkyl or aryl), $CO_2R_4$ ($R_4$ being H or alkyl), an amide, tetrazole, alkyl, hydroxyalkyl, $CW_3$ or W (W being halogen), and CN.

2. A pharmaceutical composition as claimed in claim 1 wherein any alkyl or alkoxy group present in the benzimidazole compound contains 1–6 carbon atoms.

3. A pharmaceutical composition as claimed in claim 1 wherein

R represents a substituted phenyl group having the structural formula II

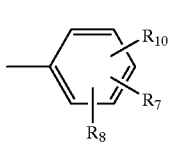

II wherein $R_1$, $R_2$ and $R_9$ are each selected idependently from the group consisting of H, $NO_2$, $N_3$, $NHCOR_3$ ($R_3$ being alkyl or aryl), $CO_2R_4$ ($R_4$ being H or alkyl), an amide, tetrazole, alkyl, hydroxyalkyl, $CW_3$ or W (W being halogen), and CN, subject to the proviso that $R_1$, $R_2$ and $R_9$ are not each hydrogen.

4. A pharmaceutical composition as claimed in claim 3 wherein $R_1$ is a group other than hydrogen and is in the 4'-position, and wherein $R_2$ and $R_9$ are each hydrogen.

5. A pharmaceutical composition as claimed in claim 1 wherein

R' represents an optionally substituted phenyl group having the structural formula III:

III wherein $R_7$, $R_8$ and $R_{10}$ are each selected independently from the group consisting of H, hydroxy, alkoxy, $NO_2$, $N_3$, $NR_5R_6$ ($R_5$ and $R_6$ each being independently hydrogen, alkyl or alkoxy), $NHCOR_3$ ($R_3$ being alkyl or aryl), $CO_2R_4$ ($R_4$ being H or alkyl), an amide, tetrazole, alkyl, hydroxyalkyl, $CW_3$ or W (W being halogen), and CN.

6. A pharmaceutical composition as claimed in claim 5 wherein $R_7$ is a group other than hydrogen and is in the 4'-position, and wherein $R_8$ and $R_{10}$ are each hydrogen.

7. A pharmaceutical composition as claimed in claim 1 wherein R' is hydrogen or alkyl and R is a phenyl group having at least one substituent in the benzene ring selected from the group consisting of $NO_2$, $N_3$, $NHCOR_3$ ($R_3$ being alkyl or aryl), CO₂R₄ (R₄ being H or alkyl), an amide, tetrazole, alkyl, hydroxyalkyl, CW₃ or W (W being halogen), and CN.

8. A pharmaceutical composition as claimed in claim 1 wherein said benzimidazole compound is selected from the group consisting of the following:

benzimidazole4-carboxamide;
2-(4'-trifluoromethylphenyl)benzimidazole-4-carboxamide;
2-(4'-nitrophenyl)benzimidazole-4-carboxamide;
2-(4'-cyanophenyl)benzimidazole-4-carboxamide;
2-(3'-trifluoromethylphenyl)benzimidazole4-carboxamide; and
2-(2'-trifluoromethylphenyl)benzimidazole-4-carboxamide.

9. A pharmaceutical composition as claimed in claim 1 wherein said benzimidazole compound is in the form of a pro-drug having a substituent group selected from the group consisting of phosphate, carbamate and amino acid.

10. A compound having the structural formula I

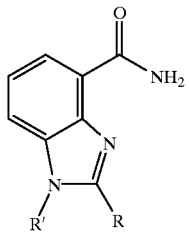

or a pharmaceutically acceptable salt thereof, wherein

R is selected from the group consisting of hydrogen, hydroxyalkyl and a phenyl group which is substituted by one or more substituents in the benzene ring selected from the group consisting of NO₂, N₃, NHCOR₃ (R₃ being alkyl or aryl), CO₂R₄ (R₄ being H or alkyl), an amide, tetrazole, alkyl, hydroxylalkyl, CW₃ or W (W being halogen), and CN R' is selected from the group consisting of hydrogen, alkyl, hydroxyalkyl, acyl and an optionally substituted phenyl group having the structural formula III

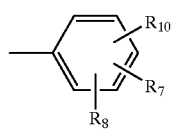

wherein R₇, R₈ and R₁₀ are each selected independently from the group consisting of H, hydroxy, alkoxy, NO₂, N₃, NR₅R₆ (R₅ and R₆ each being independently hydrogen, alkyl or alkoxy), NHCOR₃ (R₃ being alkyl or aryl), CO₂R₄ (R₄ being H or alkyl), an amide, tetrazole, alkyl, hydroxylalkyl, CW₃ or W (W being halogen), and CN.

11. A compound as claimed in claim 10 wherein any alkyl or alkoxy group present contains 1–6 carbon atoms.

12. A compound as claimed in claim 10 wherein

R represents a phenyl group having the structural formula II

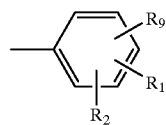

wherein R₁, R₂ and R₉ are each selected independently from the group consisting of hydrogen, NO₂, NHCOR₃ (R₃ being alkyl or aryl), CO2R₄ (R₄ being H or alkyl), an amide, tetrazole, alkyl, hydroxyalkyl, CW₃ or W (W being halogen), and CN, subject to the proviso that R₁, R₂ and R₉ are not each hydrogen.

13. A compound as claimed in claim 12 wherein R₁ is a group other than hydrogen and is in the 4'-position, and wherein R₂ and R₉ are each hydrogen.

14. A compound as claimed in claim 10 wherein R₇ is a group other than hydrogen and is in the 4'-position, and wherein R₈ and R₁₀ are each hydrogen.

15. A compound as claimed in claim 10 wherein R' is hydrogen and R represents a phenyl group having at least one substituent in the benzene ring, which substituent is selected from the group consisting of NO₂, N₃, NHCOR₃ (R₃ being alkyl or aryl), CO₂R₄ (R₄ being H or alkyl), an amide, tetrazole, alkyl, hydroxyalkyl, CW₃ or W (W being halogen), and CN.

16. A benzimidazole compound which is one of the following:

2-(4'-trifluoromethylphenyl)benzimidazole-4-carboxamide;
2-(4'-nitrophenyl)benzimidazole-4-carboxamide;
2-(4'-cyanophenyl)benzimidazole-4-carboxamide;
2-(3'-trifluoromethylphenyl)benzimidazole-4-carboxamide; or
2-(2'-trifluoromethylphenyl)benzimidazole-4-carboxamide.

17. A pharmaceutical composition comprising an effective poly(ADP-ribose)polymerase or PARP enzyme inhibiting amount of a benzimidazole compound having the structural formula I

or a pharmaceutically acceptable salt and/or pro-drug form thereof, together with a pharmaceutically acceptable carrier, wherein R is selected from the group consisting of hydrogen, alkyl, hydroxyalkyl and benzyl and phenyl groups which are unsubstituted or substituted with at least one substituent in the benzene ring selected from the group consisting of hydroxy, alkoxy, NO₂, N₃, NR₅R₆ (R₅ and R₆ each being independently hydrogen, alkyl or alkoxy), NHCOR₃ (R₃ being alkyl or aryl), CO₂R₄ (R₄ being H or alkyl), an amide, tetrazole, alkyl, hydroxyalkyl, CW₃ or W (W being halogen), and CN, and R' is selected from the group consisting of hydrogen, alkyl, hydroxyalkyl, acyl and an optionally substituted phenyl group having the structural formula III:

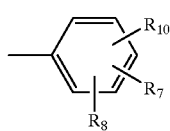

wherein $R_7$, $R_8$ and $R_{10}$ are each selected independently from the group consisting of H, hydroxy, alkoxy, $NO_2$, $N_3$, $NR_5R_6$ ($R_5$ and $R_6$ each being independently hydrogen, alkyl or alkoxy), $NHCOR_3$ ($R_3$ being alkyl or aryl), $CO_2R_4$ ($R_4$ being H or alkyl), an amide, tetrazole, alkyl, hydroxyalkyl, $CW_3$ or W (W being halogen), carboxybenzyl, and CN, said pharmaceutical composition being in the form of a sterile liquid preparation for parenteral use.

18. A pharmaceutical composition as claimed in claim 17 presented in unit dosage form and contained in sealed ampoules ready for use.

19. A pharmaceutical composition comprising a solution in phosphate buffered saline of an effective and non-toxic poly(ADP-ribose)polymerase or PARP enzyme inhibiting amount of a benzimidazole compound having the structural formula I

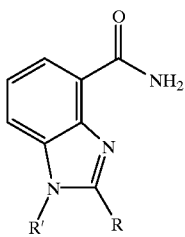

or of a pharmaceutically acceptable salt and/or pro-drug form thereof,
wherein
R is selected from the group consisting of hydrogen, alkyl, hydroxyalkyl and benzyl and phenyl groups which are unsubstituted or substituted with one or more substituents in the benzene ring selected from the group consisting of hydroxy, alkoxy, $NO_2$, $N_3$, $NR_5R_6$ ($R_5$ and $R_6$ each being independently hydrogen, alkyl or alkoxy), $NHCOR_3$ ($R_3$ being alkyl or aryl), $CO_2R_4$ ($R_4$ being H or alkyl), an amide, tetrazole, alkyl, hydroxyalkyl, $CW_3$ or W (W being halogen), and CN, and R' is selected from the group consisting of hydrogen, alkyl, hydroxyalkyl, acyl and an optionally substituted phenyl group having the structural formula III:

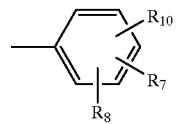

wherein $R_7$, $R_8$ and $R_{10}$ are each selected independently from the group consisting of H, hydroxy, alkoxy, $NO_2$, $N_3$, $NR_5R_6$ ($R_5$ and $R_6$ each being independently hydrogen, alkyl or alkoxy), $NHCOR_3$ ($R_3$ being alkyl or aryl), $CO_2R_4$ ($R_4$ being H or alkyl), an amide, tetrazole, alkyl, hydroxyalkyl, $CW_3$ or W (W being halogen), carboxybenzyl, and CN.

20. A pharmaceutical composition as claimed in claim 17 or 19 wherein said benzimidazole compound is selected from the group consisting of the following:

2-methylbenzimidazole-4-carboxamide;
benzimidazole-4-carboxamide;
2-phenylbenzimidazole4-carboxamide;
2-(4'-methoxyphenyl)benzimidazole-4-carboxamide;
2-(4'-trifluoromethylphenyl)benzimidazole-4-carboxamide;
2-(4'-hydroxyphenyl)benzimidazole-4-carboxamide;
2-(4'-methoxyphenyl)-N-methylbenzimidazole-4-carboxamide;
2-(4'-nitrophenyl)benzimidazole-4-carboxamide;
2-(4'-cyanophenyl)benzimidazole-4-carboxamide;
2-(3'-trifluoromethylphenyl)benzimidazole-4-carboxamide;
2-(3'-methoxyphenyl)benzimidazole-4-carboxamide;
2-(4'-methoxyphenyl)-1-N-benzoylbenzimidazole-4-carboxamide;
2-(4'-aminophenyl)benzimidazole-4-carboxamide;
2-(2'-trifluoromethylphenyl)benzimidazole-4-carboxamide; and
N-carboxybenzyl-2-(4'-methoxyphenyl)-benzimidazole-4-carboxamide.

21. A pharmaceutical composition according to claim 1 formulated for administration by intravenous injection.

* * * * *